United States Patent [19]
Mamone

[11] Patent Number: 5,827,716
[45] Date of Patent: Oct. 27, 1998

[54] MODIFIED POL-II TYPE DNA POLYMERASES

[75] Inventor: Joseph A. Mamone, Parma, Ohio

[73] Assignee: Amersham Life Science, Inc., Cleveland, Ohio

[21] Appl. No.: 688,649

[22] Filed: Jul. 30, 1996

[51] Int. Cl.$^6$ .............................. C12N 9/12; C12N 9/22
[52] U.S. Cl. ......................................... 435/194; 435/199
[58] Field of Search ..................... 435/194, 199

[56] References Cited

U.S. PATENT DOCUMENTS

| | | | |
|---|---|---|---|
| 4,889,818 | 12/1989 | Gelfand et al. | 435/194 |
| 4,942,130 | 7/1990 | Tabor et al. | 435/194 |
| 4,994,372 | 2/1991 | Tabor et al. | 435/6 |
| 5,352,778 | 10/1994 | Comb et al. | 536/23.2 |
| 5,489,523 | 2/1996 | Mathur | 435/194 |
| 5,500,363 | 3/1996 | Comb et al. | 435/194 |

FOREIGN PATENT DOCUMENTS

| | | |
|---|---|---|
| 0 455 430 | 11/1991 | European Pat. Off. . |
| 0 547 359 | 6/1993 | European Pat. Off. . |
| 0655506 | 5/1995 | European Pat. Off. . |
| 0 701 000 | 3/1996 | European Pat. Off. . |
| 09689 | 6/1992 | WIPO . |
| 04162 | 2/1995 | WIPO . |

OTHER PUBLICATIONS

Adams, "Large Scale Growth of Hyperthermophiles," *Archaea: A Laboratory Manual*, Robb et al. editors, Cold Spring Habor Laboratory Press, Plainview, New York, pp. 47–49 (1995).
Bernard et al., "A Conserved 3'→5' Exonuclease Active Site in Prokaryotic and Eukaryotic DNA Polymerases," *Cell* 59:219–228 (1989).
Braithwaite et al., "Compilation, alignment, and phylogenetic relationships of DNA polymerases," *Nucleic Acids Research* 21:787–802 (1993).
Brinkmann et al., "High–level expression of recombinant genes in *Escherichia coli* is dependent on the availability of the dnaY gene product," *Gene* 85:109–114 (1989).
Delarue et al., "An attempt to unify the structure of polymerases," *Protein Engineering* 3(6):461–467 (1990).
Garcia et al. "The *E. coli* dnaY Gene Encodes an Arginine Transfer RNA," *Cell* 45:453–459 (1986).
Kong et al. "Characterization of a DNA Polymerase from the Hyperthermophile Archaea *Thermococcus litoralis,*" *J. Biol. Chem.* 268:1965–1975 (1993).
Reddy et al., "Hyperexpression and purification of *Escherichia coli* adenylate cyclase using a vector designed for expression of lethel gene products," *Nucleic Acids Research* 17:10473–10488 (1989).
Richardson, "DNA polymerase from *Escherichia coli*" in *Procedures in Nucleic Acid Research*, Cantoni and Davies editors, Harper and Row, New York, pp. 263–276 (1966).
Schenk et al., "Improved High–Level Expression System for Eukaryotic Genes in *Escherichia coli* Using T7 RNA Polymerase and Rare $^{Arg}$tRNAs," *BioTechniques* 19:196–200 (1995) (p. 12).
Scopes, *Protein Purification*, Springer–Verlag, New York, New York, pp. 46–48 (1994).
Uemori et al., "Organization and nucleotide sequence of the DNA polymerase gene from the archaeon *Pyrococcus furiosus,*" *Nucleic Acids Research* 21:259–256 (1993).
Uemori et al. (1993) Organization and nucleotide sequence of the DNA polymerase gene from the archaeon *Pyrococcus furiosus*, Nucleic Acids Research 21 (2): 259–265, Jan. 11, 1993.
Pisani et al. (1994) Evidence That an Archaeal α–like DNA Polymerase Has a Modular Organization of Its Associated Catalytic Activities, Journal of Biological Chemistry 269 (11): 7887–7892, Mar. 18, 1994.
Lundberg et al. (1991) High–fidelity amplification using a thermostable DNA polymerase isolated from *Phyrococcus furiosus*, Gene 108: 1–6, Sep. 1991.
Ngo et al. (1994) Computational Complexity, Protein Structure Prediction, and the Levinthal Paradox, In The Protein Folding Problem and Tertiary Structure Prediction, Eds. Merz et al., Boston, MA, Birkhauser, pp. 491–495, Jan. 1994.

*Primary Examiner*—Robert A. Wax
*Assistant Examiner*—Einar Stole
*Attorney, Agent, or Firm*—Lyon & Lyon LLP

[57] ABSTRACT

A Pol-II type DNA polymerase wherein an alanine located at the nucleotide binding site is replaced with a hydroxy containing amino acid.

7 Claims, 3 Drawing Sheets

MILDVDYITEEGKPVIRLFKKENGKFKIEHDRTFRPYIYALLRDDSKIEEVKKITG
ERHGKIVRIVDVEKVEKKFLGKPI
TVWKLYLEHPQDVPTIREKVREHPAVVDIFEYDIPFAKRYLIDKGLIPMEGEEELK
ILAFDIETLYHEGEEFGKGPIIMI
SYADENEAKVITWKNIDLPYVEVVSSEREMIKRFLRIIREKDPDIIVTYNGDSFDF
PYLAKRAEKLGIKLTIGRDGSEPK
MQRIGDMTAVEVKGRIHFDLYHVITRTINLPTYTLEAVYEAIFGKPKEKVYADEIA
KAWESGENLERVAKYSMEDAKATY
ELGKEFLPMEIQLSRLVGQPLWDVSRSSTGNLVEWFLLRKAYERNEVAPNKPSEEE
YQRRLRESYTGGFVKEPEKGLWEN
IVYLDFRALYPSIIITHNVSPDTLNLEGCKNYDIAPQVGHKFCKDIPGFIPSLLGH
LLEERQKIKTKMKETQDPIEKILL
DYRQKAIKLLANSFYGYYGYAKARWYCKECAESVTAWGRKYIELVWKELEEKFGFK
VLYIDTDGLYATIPGGESEEIKKK
ALEFVKYINSKLPGLLELEYEGFYKRGFFVTKKRYAVIDEEGKVITRGLEIVRRDW
SEIAKETQARVLETILKHGDVEEA
VRIVKEVIQKLANYEIPPEKLAIYEQITRPLHEYKAIGPHVAVAKKLAAKGVKIKP
GMVIGYIVLRGDGPISNRAILAEE
YDPKKHKYDAEYYIENQVLPAVLRILEGFGYRKEDLRYQKTRQVGLTSWLNIKKSZ

*Fig. 1*

```
ATGATTTTAGATGTGGATTACATAACTGAAGAAGGAAAACCTGTTATTAGGCTATTCAAAAAAGAGAACGGAAAATTTAA
GATAGAGCATGATAGAACTTTTAGACCATACATTTACGCTCTTCTCAGGGATGATTCAAAGATTGAAGAAGTTAAGAAAA
TAACGGGGGAAAGGCATGGAAAGATTGTGAGAATTGTTGATGTAGAGAAGGTTGAGAAAAAGTTTCTCGGCAAGCCTATT
ACCGTGTGGAAACTTTATTTGGAACATCCCCAAGATGTTCCCACTATTAGAGAAAAAGTTAGAGAACATCCAGCAGTTGT
GGACATCTTCGAATACGATATTCCATTTGCAAAGAGATACCTCATCGACAAAGGCCTAATACCAATGGAGGGGGAAGAAG
AGCTAAAGATTCTTGCCTTCGATATAGAAACCCTCTATCACGAAGGAGAAGAGTTTGGAAAAGGCCCAATTATAATGATT
AGTTATGCAGATGAAAATGAAGCAAAGGTGATTACTTGGAAAAACATAGATCTTCCATACGTTGAGGTTGTATCAAGCGA
GAGAGAGATGATAAAGAGATTTCTCAGGATTATCAGGGAGAAGGATCCTGACATTATAGTTACTTATAATGGAGACTCAT
TCGACTTCCCATATTTAGCGAAAAGGGCAGAAAAACTTGGGATTAAATTAACCATTGGAAGAGATGGAAGCGAGCCCAAG
ATGCAGAGAATAGGCGATATGACGGCTGTAGAAGTCAAGGGAAGAATACATTTCGACTTGTATCATGTAATAACAAGGAC
AATAAATCTCCCAACATACACACTAGAGGCTGTATATGAAGCAATTTTTGGAAAGCCAAAGGAGAAGGTATACGCCGACG
AGATAGCAAAAGCCTGGGAAAGTGGAGAGAACCTTGAGAGAGTTGCCAAATACTCGATGGAAGATGCAAAGGCAACTTAT
GAACTCGGGAAAGAATTCCTTCCAATGGAAATTCAGCTTTCAAGATTAGTTGGACAACCTTTATGGGATGTTTCAAGGTC
AAGCACAGGGAACCTTGTAGAGTGGTTCTTACTTAGGAAAGCCTACGAAAGAAACGAAGTAGCTCCAAACAAGCCAAGTG
AAGAGGAGTATCAAAGAAGGCTCAGGGAGAGCTACACAGGTGGATTCGTTAAAGAGCCAGAAAAGGGGTTGTGGGAAAAC
ATAGTATACCTAGATTTTAGAGCCCTATATCCCTCGATTATAATTACCCACAATGTTTCTCCCGATACTCTAAATCTTGA
GGGATGCAAGAACTATGATATCGCTCCTCAAGTAGGCCACAAGTTCTGCAAGGACATCCCTGGTTTTATACCAAGTCTCT
TGGGACATTTGTTAGAGGAAAGACAAAAGATTAAGACAAAAATGAAGGAAACTCAAGATCCTATAGAAAAAATACTCCTT
GACTATAGACAAAAAGCGATAAAACTCTTAGCAAATTCTTTCTACGGATATTATGGCTATGCAAAAGCAAGATGGTACTG
TAAGGAGTGTGCTGAGAGCGTTACTGCCTGGGGAAGAAAGTACATCGAGTTAGTATGGAAGGAGCTCGAAGAAAAGTTTG
GATTTAAAGTCCTCTACATTGACACTGATGGTCTCTATGCAACTATCCCAGGAGGAGAAAGTGAGGAAATAAAGAAAAAG
GCTCTAGAATTTGTAAAATACATAAATTCAAAGCTCCCTGGACTGCTAGAGCTTGAATATGAAGGGTTTTATAAGAGGGG
ATTCTTCGTTACGAAGAAGAGGTATGCAGTAATAGATGAAGAAGGAAAAGTCATTACTCGTGGTTTAGAGATAGTTAGGA
GAGATTGGAGTGAAATTGCAAAAGAAACTCAAGCTAGAGTTTTGGAGACAATACTAAAACACGGAGATGTTGAAGAAGCT
GTGAGAATAGTAAAAGAAGTAATACAAAAGCTTGCCAATTATGAAATTCCACCAGAGAAGCTCGCAATATATGAGCAGAT
AACAAGACCATTACATGAGTATAAGGCGATAGGTCCTCACGTAGCTGTTGCAAAGAAACTAGCTGCTAAAGGAGTTAAAA
TAAAGCCAGGAATGGTAATTGGATACATAGTACTTAGAGGCGATGGTCCAATTAGCAATAGGGCAATTCTAGCTGAGGAA
TACGATCCCAAAAAGCACAAGTATGACGCAGAATATTACATTGAGAACCAGGTTCTTCCAGCGGTACTTAGGATATTGGA
GGGATTTGGATACAGAAAGGAAGACCTCAGATACCAAAAGACAAGACAAGTCGGCCTAACTTCCTGGCTTAACATTAAAA
AATCCTAG
```

*Fig. 2*

MODIFIED POL-II TYPE DNA POLYMERASES

BACKGROUND OF THE INVENTION

The present invention relates to a DNA Pol-II polymerase to certain deletants and mutants of this enzyme, to genes and vectors encoding them and their use in DNA sequencing.

The following is a discussion of the relevant art, none of which is admitted to be prior art to the appended claims.

DNA polymerases are a family of enzymes involved in DNA repair and replication and have been classified into families sharing homologies to E. coli Pol-I, Pol-II, etc. (see Braithwaite and Ito Nuc. Acid. Res. 787, 1993). DNA polymerases have been isolated from E. coli (e.g. E. coli DNA polymerase I and E. coli polymerase II and more recently thermostable DNA polymerases have been isolated (e.g. from T. aquaticus, U.S. Pat. No. 4,889,818, and from T. litoralis).

European Patent Application 0655 506A relates to modifying DNA polymerases so that they incorporate dideoxynucleotides more efficiently. In particular, it is mentioned that the presence of a polar, hydroxy containing amino acid at a position nearing the binding site for the dNTP substrate is important for the polymerase being able to efficiently incorporate a dideoxynucleotide. Examples of Pol I type polymerases that contain such an amino acid given in the specification are T7 DNA polymerase (position 526) and E. coli DNA polymerase I and Taq DNA polymerase where the phenylalanines at position 762 and 667 respectively have been replaced by tyrosine. No examples are included of Pol II type polymerases containing such a modification although it is mentioned that such polymerases may be modified. Thermococcus litoralis, Pyrococcus furiosus and Sulfolobus solfataricus are thermostable DNA Pol-II polymerases that are mentioned as being preferred for such modification.

SUMMARY OF THE INVENTION

The present invention is based on the discovery that replacing an alanine at position 491 of Pyrococcus furiosus with tyrosine gives an enzyme that has improved incorporation of dideoxynucleotides and improved band uniformity.

Accordingly, the present invention provides a Pol-II type DNA polymerase in which A in the amino acid sequence $KN_1N_2ANN_3N_4YG$ corresponding to positions 488 to 496 of Pyrococcus furiosus has been replaced by a hydroxy containing amino acid and wherein $N_1$ is L, V, or I, $N_2$ is L, F, or Y, $N_3$ is A or S and $N_4$ is Y, F, T, S, or H.

Suitably $N_1$ is L

Suitably $N_2$ is L

Suitably $N_3$ is S

Suitably $N_4$ is F

Preferably the amino acid sequence is KLLYNSFYG.

Suitably the Pol-II type polymerase is an archaeabacterial DNA polymerase for example Pyrococcus furiosus, Thermococcus litoralis or Sulfolobus solfataricus. Preferably it is Pyrococcus furiosus.

The naturally occurring or "wild" type Pol-II DNA polymerases possess exonuclease activity, that is the ability to excise any newly synthesised bases which are incorrectly base paired to the template during chain extension. This property is disadvantageous in DNA sequencing reactions. Accordingly, in a second aspect, the present invention provides a Pol-II DNA polymerase having an amino acid sequence $KN_1N_2ANN_3N_4YG$ corresponding to positions 488 to 496 of Pyrococcus furiosus as hereinbefore defined in which the exonuclease activity is less than 50% and preferably less than 1% of the wild polymerase. This may be achieved by deleting the region responsible for exonuclease activity or by mutation of appropriate amino acid(s). It has been found that replacement of aspartate by alanine at position 215 of Pyrococcus furiosus reduces the exonuclease activity more than 1000 fold.

In addition, as it is often convenient to express the gene encoding the polymerase in E. coli, then it is preferred to incorporate codons that are highly utilised by E. coli. In the case of Pyrococcus furiosus, this can be accomplished by changing the first 58 codons in the gene to synonymous codons favoured by E. coli. In particular, it is preferred that an alanine codon be inserted at amino acid position 2.

Preferably, the Pol-II type DNA polymerase of the present invention is a purified Pol-II type DNA polymerase or fragment thereof having the DNA polymerase activity of the "wild" type enzyme. In the case of Pyrococcus furiosus this will have, preferably, at least 80% amino acid homology, preferably 90% homology, to at least a contiguous 40 amino and sequence shown in FIG. 1 (amino acid sequence of wild type Pyrococcus furiosus DNA polymerase).

In a further aspect, the present invention provides a gene encoding a Pol-II type DNA polymerase of the present invention.

When used herein, the term "a Pol-II type DNA polymerase or fragment thereof having the DNA polymerase activity of the wild type enzyme" means a DNA polymerase or fragment thereof (as hereinafter defined) which has the ability to replicate DNA with substantially the same efficiency as the wild type enzyme. By "substantially the same efficiency" is meant at least 80% and preferably at least 90% of the efficiency of the enzyme shown in FIG. 1 to incorporate deoxynucleotides.

When used herein, the term "amino acid homology" means the amino acid identity of the parent enzyme or conservative amino acid changes thereto.

By "fragment" is meant an amino-terminal deletant of the enzyme which still retains DNA polymerase activity.

The invention also encompasses a thermostable enzyme composition which comprises a purified thermostable Pol-II type DNA polymerase of the present invention.

The purified enzyme of the present invention has a molecular weight of approximately 90,000 daltons when measured on SDS-PAGE. The temperature optimum of DNA synthesis is near 75° C. under assay conditions.

The term "thermostable polymerase" means an enzyme which is stable to heat (and heat resistant) and is suitable for use in sequencing at an elevated temperature, for example 70° C. The thermostable polymerase herein must satisfy a single criterion to be effective for the sequencing reaction, i.e., the enzyme must not become irreversibly denatured (inactivated) when subjected to the elevated temperatures for the time necessary to effect the reaction. Preferably, the enzyme will not become irreversibly denatured at about 70° C. but may become denatured at higher temperatures. Preferably, the optimum temperature ranges from about 37° C. to 75° C. more preferably 65° C. to 70° C.

In addition to the deletions and amino acid changes to remove the exonuclease activity, the enzyme may have conservative amino acid changes compared with the native enzyme which do not significantly influence thermostability or enzyme activity. Such changes include substitution of like charged amino acids for one another, or amino acids with small side chains, e.g. ala for val. More drastic changes may be introduced at non-critical regions where little or no effect on polymerase activity is observed by such a change.

In yet a further aspect, the present invention provides a host cell comprising a vector containing the gene encoding the DNA sequence corresponding to a Pol-II type DNA polymerase of the present invention.

The DNA polymerases of the present invention are preferably in a purified form. By purified is meant that the DNA polymerase is isolated from a majority of host cell proteins normally associated with it; preferably the polymerase is at least 10% (w/w), e.g., at least 50% (w/w), of the protein of a preparation, even more preferably it is provided as a homogeneous preparation, e.g. homogeneous solution. Preferably the DNA polymerase is a single polypeptide on an SDS polyacrylamide gel.

Silent codon changes such as the following increase protein production in *E coli*:

substitution of the codon GAG for GAA;

substitution of the codon AGG, AGA, CGG or CGA for CGT or CGC;

substitution of the codon CTT, CTC, CTA, TTG or TTA for CTG;

substitution of the codon GGG or GGA for GGT or GGC.

The present invention also provides a method for determining the nucleotide base sequence of a DNA molecule. The method includes providing a DNA molecule; annealing with a primer molecule able to hybridize to the DNA molecule; and incubating the annealed molecules in a vessel containing at least one, and preferably four deoxynucleotide triphosphates, and a DNA polymerase of the present invention preferably one containing the alanine to tyrosine mutation. Also provided is at least one DNA synthesis terminating agent which terminates DNA synthesis at a specific nucleotide base. The method further includes separating the DNA products of the incubating reaction according to size, whereby at least a part of the nucleotide base sequence of the DNA molecule can be determined.

In preferred embodiments, the sequencing is performed at a temperature between 37° C. and 75° C., and preferably between 65° C. and 70° C.

In other preferred embodiments the Pol-II type DNA polymerase of the invention has less than 1000, 250, 100, 50, 10 or even 2 units of exonuclease activity per mg of polymerase (measured by standard procedure, see below) and is able to utilize primers having only 4, 6 or 10 bases; and the concentration of all four deoxynucleoside triphosphates at the start of the incubating step is sufficient to allow DNA synthesis to continue until terminated by the agent, e.g. a ddNTP.

Preferably, not more than a 50 fold excess of a ddNTP is provided to the corresponding dNTP.

In a related aspect, the invention features a kit or solution for DNA sequencing including a Pol-II type DNA polymerase of the present invention and a reagent necessary for the sequencing such as dITP, deaza dGTP, a chain terminating agent such as a ddNTP, and optionally a pyrophosphatase (if the ddNTP:dNTP ratio is less than 1:1).

The DNA polymerases of the present invention can be constructed using standard techniques. By way of example, in order to prepare a *Pyrococcus furiosus* polymerase with the alanine to tyrosine mutation mutagenic PCR primers can be designed to incorporate the desired Ala to Tyr codon change in a nucleic acid sequence encoding for a DNA polymerase of *Pyrococcus furiosus*. The nucleic acid sequence encoding for the wild type DNA polymerase of *Pyrococcus furiosus* is shown in FIG. 2 (SEQ. ID. NO. 38).

In another related aspect the invention features a method of sequencing a strand of DNA essentially as described above with one or more (preferably 2, 3 or 4) deoxyribonucleoside triphosphates, a Pol-II type DNA polymerase of the present invention, and a first chain terminating agent. The DNA polymerase causes the primer to be elongated to form a first series of first DNA products differing in the length of the elongated primer, each first DNA product having a chain terminating agent at its elongated end, and the number of molecules of each first DNA products being approximately the same for substantially all DNA products differing in length by no more than 20 bases. The method also features providing a second chain terminating agent in the hybridized mixture at a concentration different from the first chain terminating agent, wherein the DNA polymerase causes production of a second series of second DNA products differing in length of the elongated primer, with each second DNA product having the second chain terminating agent at its elongated end. The number of molecules of each second DNA products is approximately the same for substantially all second DNA products differing in length from each other by from 1 to 20 bases, and is distinctly different from the number of molecules of all the first DNA products having a length differing by no more than 20 bases from that of said second DNA products.

In preferred embodiments, three or four such chain terminating agents can be used to make different products and the sequence reaction is provided with a magnesium ion, (e.g. at a concentration between 0.05 and 100mM, preferably between 1 and 10 mM); and the DNA products are separated according to molecular weight in four or less lanes of a gel.

In another related aspect, the invention features a method for sequencing a nucleic acid by combining an oligonucleotide primer, a nucleic acid to be sequenced, between one and four deoxyribonucleoside triphosphates, a Pol-II type DNA polymerase of the present invention, and at least two chain terminating agents in different amounts, under conditions favouring extension of the oligonucleotide primer to form nucleic acid fragments complementary to the nucleic acid to be sequenced. The agents are differentiated from each other by intensity of a label in the primer extension products.

Other features and advantages of the invention will be apparent from the following description of the preferred embodiments thereof, and from the claims.

DESCRIPTION OF THE PREFERRED EMBODIMENT

Figure 3:
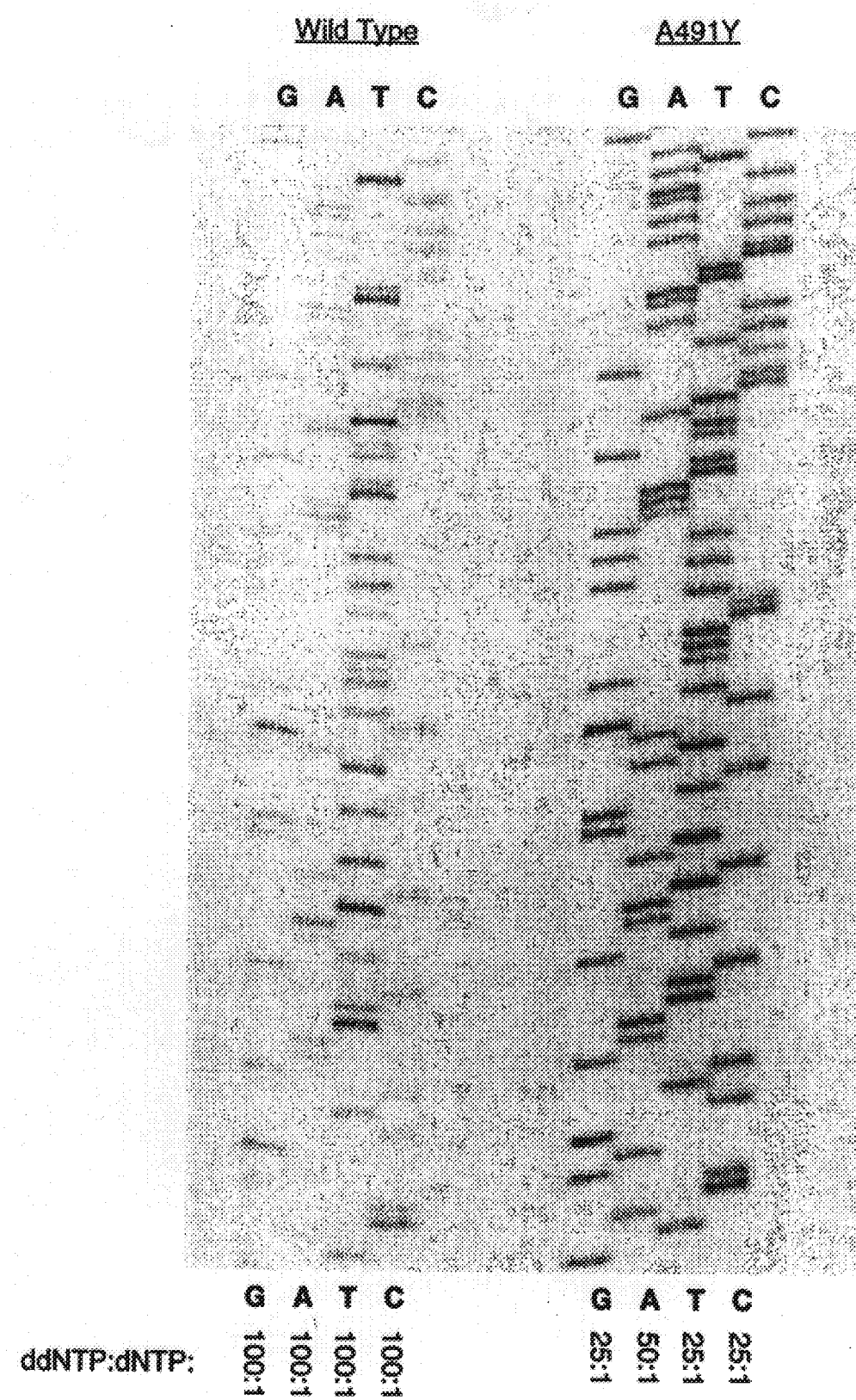

The drawings will first be briefly described.
Drawings FIG. 1 shows the amino acid sequence of wild type DNA polymerase of *Pyrococcus furiosis* (SEQ. ID. NO. 37).

FIG. 2 shows the nucleic acid sequence of wild type DNA polymerase of *Pyrococcus furiosis* (SEQ. ID. NO. 38).

FIG. 3 is a representation of a sequencing gel from reactions using wild type or A491Y Pfu polymerase.

EXAMPLES

The following examples serve to illustrate the DNA polymerases of the present invention and their use in sequencing.

Assay of DNA Polymerase Activity

DNA polymerase activity was assayed by measuring the amount of incorporation of a radiolabeled deoxynucleotide into acid precipitable material using activated salmon sperm DNA as a template (Richardson, C. C. (1966) DNA polymerase from *Escherichia coli*, pp. 263–276 In G. L. Cantoni and D. R. Davies (ed.), *Procedures in nucleic acid research*.

Harper and Row, New York). A unit of DNA polymerase is the amount of enzyme that catalyzes incorporation of 10 nmoles of deoxynucleotide triphosphate into acid-precipitable material in 30 minutes at 70° C. An assay consists of 2–10 μl of protein solution containing DNA polymerase being incubated with 50 μl of assay mix (20 mM Tris HCl pH 8.5 @ room temperature, 10 mM KCl, 10 mM $(NH_4)_2SO_4$, 0.1% (v/v) Triton X-100, 100 μg/ml BSA, 2 mM $MgSO_4$, 200 μM each deoxynucleotide triphosphate, 0.2 mg/ml activated salmon sperm DNA, 1 μCi 3000 Ci/mmole [α-$^{33}$P] dATP) at 70° C. for 10 minutes. The reaction is stopped by adding the contents of the assay to a tube containing 1 ml each of carrier 50 μg/ml fish sperm DNA, 2 mM EDTA) and precipitant (20% (w/v) trichloroacetic acid, 2% (w/v) sodium pyrophosphate). After incubation on ice for at least 5 minutes, the solution is filtered through a glass fiber filter (e.g. GF/B, Whatman), washed with several mililiters ice-cold wash solution (1N hydrochloric acid, 100 mM sodium pyrophosphate), placed in a counting vial with aqueous liquid scintillation cocktail (e.g. Biosafe II, Research Products International Corp.) and counted in a liquid scintillation counter. DNA polymerase activity of the test solution is calculated from the measured specific activity of the assay mix. The assay has been shown to be linear between 0.01 to 0.2 units per assay reaction and only values between these were accepted as significant.

Measurement of Protein Concentration

Solution protein concentrations are measured spectrophotometrically by determining the absorbance of the test solution at a wavelength of 205 nm ($A_{205}$) (Scopes, R. K. (1994) pp. 46–48 Protein Purification. Springer-Verlag, New York). The extinction coefficient of polypeptides is taken as $E_{205}(1\ mg \cdot ml^{-1})=31$.

Assay of Exonuclease Activity

Exonuclease activity was measured as described (Kong, H., Kucera, R. B. and Jack, W., E. (1993) J. Biol. Chem. 268, 1965–1975) using, as substrate a 500 bp PCR product generated from pBR322 labeled with $^3H$ by incorporation of tritiated TTP. Exonuclease assays were performed in the same buffer (20 mM Tris HCl pH 8.5 @ room temperature, 10 mM KCl, 10 mM $(NH_4)_2SO_4$, 0.1% (v/v) Triton X-100, 100 μg/ml BSA, 2 mM $MgSO_4$) and at the same temperature (70° C.) as polymerase assays.

Example 1

Construction of expression vectors pRD and pRD2

It has been shown that overproduction by cloning of tRNA$^{arg}$ can significantly increase the expression of exogenous proteins in E. coli (Brinkmann et al., (1989) Gene 85, 109–114; Schenk et al. (1995) BioTechniques 19, 196–200). Novel expression vectors were created by cloning the gene for tRNA$^{arg}$ onto a vector with tightly-regulated inducible expression for exogenous proteins such as DNA polymerases. To construct these novel vectors, two PCR primers GGAATTCAGATCTAAAAGCCATTGACTCAGCAAG (SEQ. ID. NO. 1) and GGAATTCACATGTGACAGAGCATGCGAGGAAAAT (SEQ. ID. NO. 2) were designed to amplify the gene, promotor and terminator sequences of tRNA$^{arg}$ (argU gene) from E. coli genomic DNA. The sequence of this gene and its regulatory regions has been previously published (Garcia et al. (1986) Cell 45, 453 –459). E. coli genomic DNA was prepared from strain HMS 174 (ATCC #47001). The PCR product was cloned using the vector provided as part of the pMOS Blue T-Vector kit (Amersham Life Science), and two clones were confirmed to have the correct sequence. The argU gene was excised from this vector by means of restriction digestion with the enzyme EcoR I. This fragment was ligated to vector pRE2 (Reddy et al. (1989) Nucleic Acids Res. 17, 10473–10488) which was digested with EcoR I and dephosphorylated. Resulting plasmids were screened for the presence of the argU gene, and inserts of both orientations were obtained. The new plasmid carrying the argU gene transcribed in the same direction as the vector gene for beta-lactamase is designated pRD (SEQ. ID NO. 3); the plasmid with argU transcribed in the opposite direction is designated pRD2 (SEQ. ID. NO. 4).

Example 2

Cloning of Pyrococcus furiosus DNA polymerase

Growth of Pyrococcus furiosus

A culture of Pyrococcus furiosus was a gift of Dr. Frank T. Robb. The culture was grown at 90° C. essentially as described (Archaea: A Laboratory Manual (1995) Robb, F. T. (ed.), Cold Spring Habor Laboratory Press, Plainview, N.Y.). The medium contained: per liter, 5 g Tryptone, 1 g yeast extract, 24 g NaCl, 4 g $Na_2SO_4$, 0.7 g KCl, 0.2 g $NaHCO_3$, 0.1 g KBr, 30 mg $H_3BO_3$, 10.8 g $MgCl_2.6H_2O$, 1.5 g $CaCl_2$, 25 mg $SrCl_2$, 0.4 mg resazurin.

Preparation of Genomic DNA

Frozen cell paste of Pyrococcus furiosus (approximately 350 mg) was resuspended in 700 μl of lysis buffer (50 mM Tris.HCl pH 8.0, 50 mM EDTA, 3% SDS (w/v), 1% 2-mercaptoethanol (v/v)) and incubated for 1 hour at 65° C. This solution was extracted three times with 25:24:1 phenol:chloroform:isoamyl alcohol, twice with chloroform and precipitated with two volumes of 100% ethanol. The pellet was dried briefly in vacuo and dissolved in 700 μl TE (10 mM Tris.HCl pH 8.0, 1 mM EDTA). The concentration of genomic DNA was determined spectrophotometrically by measuring the absorbance at 260 nm ($1A^{260}$=50 μg/ml) and by comparison of UV fluorescence of bands on an ethidium bromide stained agarose gel relative to standard concentration markers.

PCR Amplification of DNA polymerase Gene and Cloning

PCR primers to amplify the DNA polymerase gene from the genome of Pyrococcus furiosus were designed from the published gene sequence (Uemori, T., Ishino, Y., Toh, H., Asada, F. and Kato, I. (1993) Nucleic Acids Res. 21, 259–265) (SEQ. ID. NO. 38). The 5' primer, PFUPOLF (GGGGTACCATATGATTTTAGATGTGGATTACATA AC)(SEQ. ID. NO. 5) hybridizes to nucleotides 1–26 of the DNA polymerase coding sequence and introduces a unique Nde I (CATATG) site on the amplified product. The 3' primer, PFUPOLR2 (TCCCCCGGGCTAGGATTTTTTAATGTTAAGCCA) (SEQ. ID. NO. 6) hybridizes to nucleotides 2305–2328 of the DNA polymerase coding sequence and introduces a unique Sma I site (CCCGGG) on the amplified product.

To minimize errors introduced by Taq DNA polymerase during PCR, a modified "long PCR" was carried out. The PCR reaction contained: 20 mM Tricine (pH 8.8), 85 mM KOAc, 200 μM each dNTP, 5% DMSO, 0.5 mM each primer, 1.5 mM MgOAc (added last as hot-start), 2.5 units Hot Tub DNA polymerase per 100 μl reaction (Amersham), 0.025 U Deep Vent DNA polymerase per 100 μl reaction (New England Biolabs) and 20–100 ng Pyrococcus furiosus genomic DNA per 100 μl reaction. The cycling parameters consisted of: 94° C. 30 seconds, then 68° C. 10 minutes 40 seconds×8 cycles; 94° C. 30 seconds, then 68° C. 12 minutes×8 cycles; 94° C. 30 seconds, then 68° C. 13 minutes 20 seconds×8 cycles; 94° C. 30 s, then 68° C. 14 minutes 40 seconds×8 cycles.

The resulting PCR product was digested with Nde I and Sma I and cloned into similarly digested pRE2 (Reddy, P., Peterkofsky, A. and McKenney, K. (1989) Nucleic Acids Res. 17, 10473–10488) to produce pRE2PFUWT. Constructs made with pRE based vectors were propagated in *E. coli* strain DH-1 λ+(λcI+). The cloned gene was verified by DNA sequencing.

Example 3
Modification of the Polymerase Gene
Construction of D215A (exonuclease deficient) polymerase gene Based on alignments of DNA polymerases (Delarue, M., Poch, O., Tordo, N., Moras, D. and Argos, P. (1990) Protein Engineering 3, 461–467; Braithwaite, D. K. and Ito, J. (1993) Nucleic Acids Res. 21, 787–202), the aspartic acid at amino acid position 215 was identified as being homologous to Asp66 of ø29 DNA polymerase. An acidic residue is highly conserved at this position among DNA polymerases possessing 3'-5' exonuclease activity. Mutation of Asp66 in ø29 DNA polymerase to alanine (D66A) resulted in a polymerase which had exonuclease activity reduced about 1000-fold relative to the wild type enzyme without affecting DNA polymerase activity (Bernard, A., Blanco, L., Lβzaro, J., Martin, G. and Salas, M. (1989) Cell 59, 219–228). To accomplish the analogous mutation in the *Pyrococcus furiosus* DNA polymerase gene, two primers were made. Primer D214ABAM (AAGGATCCTGACATTATAGTTACTT ATAATGGAGACTCATTCGCCTTCCC) (SEQ. ID. NO. 7) covers the BamH I site at nt 603 of the coding sequence and is mutagenic for the Asp215 codon at nt 644 (GAC->GCC). Primer D214AECO (GGAATTCTTTCCCGAGTT CATAAG) (SEQ. ID. NO. 8) covers the EcoR I site at nt 973. These primers were used in PCR to simultaneously amplify the region between them and introduce the mutation. The resulting PCR product was digested with EcoR I and BamH I and subcloned into pRE2PFUWT to produce pTM100.

Modification of 5' end of DNA polymerase gene

In order to favor high-level expression of the DNA polymerase gene in *E. coli*, the 5' end of the gene was modified in two ways. Firstly, since the codon utilization of *Pyrococcus furiosus* differs significantly from that of *E. coli*, the first 58 codons of the gene were changed to synonymous codons favored by *E. coli* for highly expressed genes. Secondly, to further mimic a highly expressed *E. coli* coding sequence, an alanine codon (GCT) was inserted after the initiating methionine. Two long oligonucleotides, MOD95F (GCTATCCTGGACGTTGACTACATCACCGAAGAAG GTAAGCCGGTTATCCGTCTGT TCAAAAAA- GAAAACGGTAAATTCAAAATCGAACAC GACCG)(SEQ. ID. NO. 9) and MOD95R (ACCGGTGATTTTTTTAACTTCTTCGATTTAGAGTC GTCACGCAGCAGAGCGTAG ATGTACGGACGGAAG- GTACGGTCGTGTTCGATTTTG AATT)(SEQ. ID. NO. 10) which are antiparallel at their 3' ends were used together with primers MOD37F (GGGGTACCATATGGCTATCCTGGACGTTGACTACA TC)(SEQ. ID. NO. 11) and MOD32R (GGGGTACCACCGGTGATTTTTTTAACTTCTTC) (SEQ. ID. NO. 12) in a PCR reaction containing 17.5 nM each MOD95F and MOD95R and 500 nM each MOD37F and MOD32R. The resulting 189 bp product contained an Nde I site corresponding to the start of the coding sequence, the changed codons discussed above and a silent Age I site. The product was cloned into pMOSBlue PCR product cloning vector (Amersham) to produce plasmid pTM101 and verified by sequencing. To introduce an Age I site into the gene, PCR was carried out using the unmodified clone (pTM100) as template with primers AGEIMUT (AAATAACCGGTGAACGTCATGGAAAGATTGTG) (SEQ. ID. NO. 13) which introduces a silent mutation for the Age I site and R467 (CCTTTGCTTCATTTTCATCTG) (SEQ. ID. NO. 14). The resulting 350 bp PCR product was cloned into pMOSBlue to produce plasmid pTM102. The modified gene was constructed by ligating the 165 bp fragment of pTM101 digested with Nde I and Age I, the 165 bp fragment of pTM102 digested with Age I and BstB I and the >5 kb fragment of pRE2PFUWT (for exo+) or pTM100 (for exo-) digested with Nde I and BstB I. The resulting exo+ construct is designated pTM103, the exo- construct pTM104. Constructs were verified by restriction digestion with each enzyme used in cloning.

Introduction of Xho I and BssH II cloning sites

Twelve cassette oligonucleotides, six for the sense strand and six for the antisense, which match the sequence of the region between the EcoN I (nt 1309 of the modified coding sequence) and Sac I (nt 1585) restriction sites except for silent mutations which introduce Xho I and BssH II sites at nts 1372 and 1507, respectively, were constructed. The cassette oligos are:

CASST1(AGTAGGCCACAAGTTCTGCAAGGACAT CCCTGGTTTTATACCAAGTCTCT)(SEQ. ID. NO. 15),

CASST2(TGGGACATTTGCTCGAGGAAAGACAA AAGATTAAGACAAAAATGAAGGAA)(SEQ. ID. NO. 16),

CASST3(ACTCAAGATCCTATAGAAAAAATACTC CTTGACTATAGACAAAAAGCGAT)(SEQ. ID. NO. 17),

CASST4(AAAACTCTTAGCAAATTCTTTCTACGG ATATTATGGCTATGCAAAAGCGC)(SEQ. ID. NO. 18),

CASST5(GCTGGTACTGTAAGGAGTGTGCTGA GAGCGTTACTGCCTGGGAAGAAAG)(SEQ. ID. NO. 19),

CASST6(TACATCGAGTTAGTATGGAAGGAGCT) (SEQ. ID. NO. 20),

CASSB1(CCTTCCATACTAACTCGATGTACTTTC TTCCCCAGGCAGTAACGCTCTCA)(SEQ. ID. NO. 21),

CASSB2(GCACACTCCTTACAGTACCAGCGCGC TTTTGCATAGCCATAATATCCGTA)(SEQ. ID. NO. 22),

CASSB3(GAAAGAATTTGCTAAGAGTTTTATCG CTTTTTGTCTATAGTCAAGGAGTA)(SEQ. ID. NO. 23),

CASSB4(TTTTTTCTATAGGATCTTGAGTTTCCT TCATTTTTGTCTTAATCTTTTGT)(SEQ. ID. NO. 24),

CASSB5(CTTTCCTCTAACAAATGTCCCAAGAG ACTTGGTATAAAACCAGGGATGTC)(SEQ. ID. NO. 25) and

CASSB6 (CTTGCAGAACTTGTGGCCTAC)(SEQ. ID. NO. 26).

Oligonucleotides were purchased 5' phosphorylated using Phosphalink amidite (ABI). Each oligonucleotide was made 20 μM in TE (10 mM Tris.HCl pH 8.0, 0.1 mM EDTA). In one reaction, 2 μl of each oligonucleotide were combined with 3 μl 10× Taq ligase buffer and 1 μl (40 units) Taq DNA ligase (New England Biolabs) and incubated 30 minutes at 45° C. PCR was carried out using 1 μl of this ligated material as substrate and primers CASPCRF2 (TCGCTCCTCAAGTAGGCCACAAGTTCTGCAAGGAC ATCCC)(SEQ. ID. NO. 27) and CASPCRR2 (TCTTCGAGCTCCTTCCATACTAACTCGATGTACTTT CTTC)(SEQ. ID. NO. 28). The resulting product was digested with Sac I and EcoNI and cloned into similarly digested parent vector pTM103 to produce pTM119 or the same construct in pRD to produce pTM118.

Example 4
Expression and Purification of Pfu DNA polymerase

Expression

E. coli strain M5248 (cI857 lysogen) harboring the expression plasmid was cultured in LB medium (per liter: 10 g tryptone, 5 g yeast extract, 10 g NaCl) supplemented with 50 µg/ml ampicillin. The culture was grown at 30–32° C. until the $OD_{600}$ reached approximately 1.0 at which time the culture temperature was raised to 40°–42° C. Growth continued at this temperature for 2 hours. The cells were harvested and frozen at -20° C. until needed.

Preparation of Extract

Frozen cell paste was resuspended in buffer A (50 mM Tris.HCl pH 8.0, 1 mM EDTA, 0.1% (v/v) each, NP40 and Tween-20) containing 100 mM NaCl, 1 mM PMSF, lysozyme (0.2 mg·ml$^{-1}$) and DNase I (10 µg·ml$^{-1}$) at 0.1 ml buffer per ml original culture volume. After 15 minutes incubation at room temperature, the lysate was subjected to brief sonication, and cleared by centrifugation. The cleared lysate was heated to 70° C. for 10–15 minutes, incubated on ice for 10 minutes and centrifuged again. This heat treatment inactivates detectable DNA polymerase activity resulting from the E. coli host polymerases. The cleared, heat-treated lysate is designated fraction I.

Liquid Chromatography Purification

Fraction I was passed through a column of DEAE cellulose (DE-52, Whatman) equilibrated in buffer A containing 100 mM NaCl and washed with the same buffer. The flow-through fractions containing DNA polymerase activity were collected and loaded onto a column of Heparin Sepharose (Heparin Sepharose CL-6B, Pharmacia) equilibrated in the same buffer. The column was washed and the DNA polymerase activity was eluted with a linear salt gradient of 100–700 mM NaCl in buffer A with the peak of activity eluting at about 300 mM NaCl. The active fractions were pooled, concentrated via ultrafiltration (Centricon-50, Amicon) and dialyzed against storage buffer (50 mM Tris HCl pH 8.2 @ room temperature, 0.1 mM EDTA, 0.1% (v/v) Triton X-100, 0.1% (v/v) NP40 and 50% (v/v) glycerol).

Example 5
Mutagenesis of Pfu DNA polymerase Gene

Mutations were introduced into the coding sequence of the Pyrococcus furiosus DNA polymerase gene in a manner analogous to the cassette mutagenesis used to introduce the BssHII and Xho I restriction sites. For example, mutant A491Y was constructed as follows:

Oligonucleotides CASST1, CASST2, CASST3, CASST5, CASST6, CASSB1, CASSB2, CASSB4, CASSB5, CASSB6 described above were combined with two mutagenic oligonucleotides, A491YT (AAAACTCTTATACAATTCTTTCTACGGATATTATGG CTATGCAAAAGCGC) SEQ. ID. NO. 29) and A491YB (GAAAGAATTGTATAAGAGTTTTATCGCTTTTTGTCT ATAGTCAAGGAGTA) (SEQ. ID. NO. 30), both 5' phosphorylated as above to a final concentration of 1.7 µM each oligonucleotide in TE (10 mM Tris.HCl pH 8.0, 0.1 mM EDTA). These two primers are identical to CASST4 and CASSB3, respectively, except the codon for alanine 491 (GCA) has been changed to tyrosine (TAC). To 48 µl of the oligonucleotide mix was add 8.5 µl of annealing buffer (50 mM MgCl$_2$, 100 mM Tris.HCl pH 7.5 and 300 mM NaCl). The mixture was heated to 100° C. and slow cooled to 50° C. at which time 8 µl was withdrawn and added to 1 µl Taq DNA ligase buffer and 1 µl (40 units) Taq DNA ligase (New England Biolabs). Incubation continued for 30 minutes at 50° C. PCR was carried out with Ultma DNA polymerase (Perkin-Elmer) using 1 µl of this ligated material as template and oligonucleotides CASST1 and CASSB1 as PCR primers. The resulting 275 bp product was extracted with CHCl$_3$, digested with Xho I and BssH II, and cloned into similarly digested pTM118 to produce pTM113.

In a similar fashion, three other mutants were constructed. Using oligonucleotides N492YT (AAAACTCTTAGCA TACTCTTTCTACGGATATTATGGCTATGCAAAAGCG C) SEQ. ID. NO. 31) and N492YB (GAAAGAGT ATGCTAAGAGTTTTATCGCTTTTTGTCTATAGTCAA GGAGTA) SEQ. ID. NO. 32), a construct was made which has tyrosine substituted for asparagine 492 (N492Y). Using oligonucleotides 0491YT (AAAACTCTTAGCATACAATTC TTTCTACGGATATTATGGCTATGCAAAAGCGC) SEQ. ID. NO. 33) and 0491YB (GAAAGAATTGTATGCTA AGAGTTTTATCGCTTTTTGTCTATAGTCAAGGAGTA) SEQ. ID. NO. 34), a construct was made which has tyrosine inserted between alanine 491 and asparagine 492 (ω491Y). Using oligonucleotides OTAQ7T (AAAAACCATCAACTACGGTGTTCTCTACGGATATTA TGGCTATGCAAAAGCGC) SEQ. ID. NO. 35) and OTAQ7B (GAGAACACCGTAGTTGATGGTTTTT ATCGCTTTTTGTCTATAGTCAAGGAGTA) SEQ. ID. NO. 36), a construct was made which has the sequence of seven amino acids TINYGVL replacing the sequence of six amino acids LLANSF at position #490–495 of the Pyrococcus furiosus DNA polymerase coding sequence (ωTAQ7).

Example 6
Characterization of Pfu DNA polymerases

Mutant DNA polymerases were characterized by performing sequencing reactions. The reaction contained annealed primer:template (0.5 pmole universal cycle primer (Amersham) labeled on the 5' end by the action of T4 polynucleotide kinase and [γ-$^{33}$p] ATP annealed to 1 µg M13mp18) in reaction buffer (20 mM Tris HCl pH 8.5 @ room temperature, 10 mM KCl, 10 mM $(NH_4)_2SO_4$, 0.1% (v/v) Triton X-100, 100 µg/ml BSA, 2 mM $MgSO_4$) and 4–8 units of polymerase. This mixture was divided into four and added to tubes containing 4 µl termination mix. All termination mixes consisted of 50 µM each dNTP in reaction buffer and various amounts of ddNTP. A complement of termination mixes at 100:1 ddNTP:dNTP, for example, contained 5 mM ddG, ddA, ddT or ddC in addition to the dNTPs and buffer. Upon addition of the enzyme primer-:template to the termination mixes, the reactions were incubated at 70° C. for 15–30 minutes, stopped by addition of 4 µl stop solution (95% formamide, 10 mM EDTA, 0.1% each bromophenol blue and xylene cyanol), heated to ca. 75° C. for 5 minutes and loaded onto a denaturing polyacrylamide gel and electrophoresed under standard conditions. An autoradiogram of the electrophoresed gel was subjected to densitometry with an optical scanner (SciScan, USB) to determine band intensity.

Wild type Pyrococcus furiosus DNA polymerase requires termination mixes that are 100:1 ddNTP:dNTP to bring about chain termination events distributed evenly in the region 1–400 nt downstream of the primer. The root mean square ("RMS value") of the measured band intensities in the region about 50–200 nt downstream of the primer is approximately 0.65. In other words, the standard deviation of the measured band intensities is 65% of the mean value.

The mutant enzyme A491Y DNA polymerase required termination mixes adjusted to 25:1, 50:1, 25:1 and 25:1 ddNTP:dNTP for G, A, T and C, respectively, to bring about chain termination events distributed evenly in the region 1–400 nt downstream of the primer. Using the same ratios as wild type (100:1 ddNTP:dNTP) resulted in very short extension products i.e. less than 40 from the primer. Therefore, the A491Y mutant is able to utilize ddNTPs more efficiently than the wild type enzyme. More significantly, the band intensities on the autoradiogram of an optimized reaction are much more uniform for the A491Y mutant DNA polymerase than for the wild type DNA polymerase having and RMS value of 0.3. This RMS value reflects a great improvement in band uniformity. FIG. 3 shows sequencing data produced by wild type and A491Y DNA polymerases.

The mutant enzymes ω491Y (tyrosine inserted between A491 and N492), ωTAQ7 (amino acids 489–494 replaced with 7 corresponding amino acids from Taq polymerase including an F->Y substitution) and N492Y were purified and all had significantly reduced specific activities (greater than 100-fold of wild type).

Other embodiments are within the following claims.

I claim:

1. A Pol-II type DNA polymerase wherein an alanine located at a nucleotide binding site corresponding to amino acid residues 488 to 496 of *Pyrococcus furiosus* is replaced with a hydroxy containing amino acid.

2. The polymerase of claim 1, wherein said polymerase is obtained from an organism selected from the group consisting of *Pyrococcus furiosus, Thermococcus litoralis* and *Sulfolobus solfataricus*.

3. The polymerase of claim 1, wherein exonuclease activity of said polymerase is less than 50% of wildtype polymerase exonuclease activity.

4. The polymerase of claim 1, wherein exonuclease activity of said polymerase is less 1% of wildtype polymerase exonuclease activity.

5. An enzymatically active Pol-II type DNA polymerase or enzymatically active fragment thereof comprising the sequence $KN_1N_2ANN_3N_4YG$ corresponding to positions 488 to 496 of *Pyrococcus furiosus* wherein A has been replaced with a hydroxy containing amino acid, and wherein $N_1$ is L, V or I, $N_2$ is L, F, or Y, $N_3$ is A or S, and $N_4$ is Y, F, T, S, or H.

6. An enzymatically active Pol-II type DNA polymerase or enzymatically active fragment thereof of *Pyrococcus furiosus* wherein alanine 491 has been replaced with tyrosine.

7. Thermostable enzyme compositions comprising a purified thermostable Pol-II type DNA polymerase of any of claims 1, 2, 3, 4, 5, or 6.

* * * * *

SEQUENCE LISTING ( 1 ) GENERAL INFORMATION:

( i i i ) NUMBER OF SEQUENCES: 38

( 2 ) INFORMATION FOR SEQ ID NO: 1:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( x i ) SEQUENCE DESCRIPTION: SEQ ID NO: 1:

GGAATTCAGA TCTAAAAGCC ATTGACTCAG CAAG                                        34

( 2 ) INFORMATION FOR SEQ ID NO: 2:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( x i ) SEQUENCE DESCRIPTION: SEQ ID NO: 2:

GGAATTCACA TGTGACAGAG CATGCGAGGA AAAT                                        34

( 2 ) INFORMATION FOR SEQ ID NO: 3:

( i ) SEQUENCE CHARACTERISTICS:
( A ) LENGTH: 5249 base pairs
( B ) TYPE: nucleic acid
( C ) STRANDEDNESS: single
( D ) TOPOLOGY: linear ( x i ) SEQUENCE DESCRIPTION: SEQ ID NO: 3:

TTCACATGTG ACAGAGCATG CGAGGAAAAT AGACGACATT TTTGGTGATA ATGTCCCAAA            60

TATGTCCCAC TCTGAAATTA TGGAGGATAT AAAGAAGGCG TAACTGATTG AATTGTAATG           120

GCGCGCCCTG CAGGATTCGA ACCTGCGGCC CACGACTTAG AAGGTCGTTG CTCTATCCAA           180

CTGAGCTAAG GGCGCGTTGA TACCGCAATG CGGTGTAATC GCGTGAATTA TACGGTCAAC           240

CCTTGCTGAG TCAATGGCTT TTAGATCTGA ATTCTCATGT TTGACAGCTT ATCATCGATA           300

AGCTTTAATG CGGTAGTTTA TCACAGTTAA ATTGCTAACG CAGTCAGGCA CCGTGTATGA           360

AATCTAACAA TGCGCTCATC GTCATCCTCG GCACCGTCAC CCTGGATGCT GTAGGCATAG           420

GCTTGGTTAT GCCGGTACTG CCGGGCCTCT TGCGGGATAT CGTCCATTCC GACAGCATCG           480

CCAGTCACTA TGGCGTGCTG CTAGTCCAGT AATGACCTCA GAACTCCATC TGGATTTGTT           540

CAGAACGCTC GGTTGCCGCC GGGCGTTTTT TATTGGTGAG AATCGCAGCA ACTTGTCGCG           600

CCAATCGAGC CATGTCGTCG TCAACGACCC CCCATTCAAG AACAGCAAGC AGCATTGAGA           660

ACTTTGGAAT CCAGTCCCTC TTCCACCTGC TGACTAGCGC TATATGCGTT GATGCAATTT           720

| | | | | | |
|---|---|---|---|---|---|
| CTATGCGCAC | CCGTTCTCGG | AGCACTGTCC | GACCGCTTTG | GCCGCCGCCC | AGTCCTGCTC | 780
| GCTTCGCTAC | TTGGAGCCAC | TATCGACTAC | GCGATCATGG | CGACCACACC | CGTCCTGTGG | 840
| ATCTCTCACC | TACCAAACAA | TGCCCCCCTG | CAAAAAATAA | ATTCATATAA | AAAACATACA | 900
| GATAACCATC | TGCGGTGATA | AATTATCTCT | GGCGGTGTTG | ACATAAATAC | CACTGGCGGT | 960
| GATACTGAGC | ACATCAGCAG | GACGCACTGA | CCACCATGAA | GGTGACGCTC | TTAAAAATTA | 1020
| AGCCCTGAAG | AAGGGCAGCA | TTCAAAGCAG | AAGGCTTTGG | GGTGTGTGAT | ACGAAACGAA | 1080
| GCATTGGCCG | TAAGTGCGAT | TCCGGATTAG | CTGCCAATGT | GCCAATCGCG | GGGGGTTTTC | 1140
| GTTCAGGACT | ACAACTGCCA | CACACCACCA | AGCTAACTG | ACAGGAGAAT | CCAGATGGAT | 1200
| GCACAAACAC | GCCGCCGCGA | ACGTCGCGCA | GAGAACAGG | CTCAATGGAA | AGCAGCAAAT | 1260
| CCCCTGTTGG | TTGGGGTAAG | CGCAAAACCA | GTTCCGAAAG | ATTTTTTAA | CTATAAACGC | 1320
| TGATGGAAGC | GTTTATGCGG | AAGAGGTAAA | GCCCTTCCCG | AGTAACAAAA | AAACAACAGC | 1380
| ATAAATAACC | CCGCTCTTAC | ACATTCCAGC | CCTGAAAAAG | GGCATCAAAT | TAAACCACAC | 1440
| CTATGGTGTA | TGCATTTATT | TGCATACATT | CAATCAATTG | TTATCTAAGG | AAATACTTAC | 1500
| ATATGATATC | TAGAGGATCC | CGGGTACCGA | GCTCGTCGAC | CGATGCCCTT | GAGAGCCTTC | 1560
| AACCCAGTCA | GCTCCTTCCG | GTGGGCGCGG | GGCATGACTA | TCGTCGCCGC | ACTTATGACT | 1620
| GTCTTCTTTA | TCATGCAACT | CGTAGGACAG | GTGCCGGCAG | CGCTCTGGGT | CATTTCGGC | 1680
| GAGGACCGCT | TTCGCTGGAG | CGCGACGATG | ATCGGCCTGT | CGCTTGCGGT | ATTCGGAATC | 1740
| TTGCACGCCC | TCGCTCAAGC | CTTCGTCACT | GGTCCCGCCA | CCAAACGTTT | CGGCGAGAAG | 1800
| CAGGCCATTA | TCGCCGGCAT | GGCGGCCGAC | GCGCTGGGCT | ACGTCTTGCT | GGCGTTCGCG | 1860
| ACGCGAGGCT | GGATGGCCTT | CCCCATTATG | ATTCTTCTCG | CTTCCGGCGG | CATCGGGATG | 1920
| CCCGCGTTGC | AGGCCATGCT | GTCCAGGCAG | GTAGATGACG | ACCATCAGGG | ACAGCTTCAA | 1980
| GGATCGCTCG | CGGCTCTTAC | CAGCCTAACT | TCGATCACTG | GACCGCTGAT | CGTCACGGCG | 2040
| ATTTATGCCG | CCTCGGCGAG | CACATGGAAC | GGGTTGGCAT | GGATTGTAGG | CGCCGCCCTA | 2100
| TACCTTGTCT | GCCTCCCCGC | GTTGCGTCGC | GGTGCATGGA | GCCGGGCCAC | CTCGACCTGA | 2160
| ATGGAAGCCG | GCGGCACCTC | GCTAACGGAT | TCACCACTCC | AAGAATTGGA | GCCAATCAAT | 2220
| TCTTGCGGAG | AACTGTGAAT | GCGCAAACCA | ACCCTTGGCA | GAACATATCC | ATCGCGTCCG | 2280
| CCATCTCCAG | CAGCCGCACG | CGGCGCATCT | CGGGCAGCGT | TGGGTCCTGG | CCACGGGTGC | 2340
| GCATGATCGT | GCTCCTGTCG | TTGAGGACCC | GGCTAGGCTG | GCGGGGTTGC | CTTACTGGTT | 2400
| AGCAGAATGA | ATCACCGATA | CGCGAGCGAA | CGTGAAGCGA | CTGCTGCTGC | AAAACGTCTG | 2460
| CGACCTGAGC | AACAACATGA | ATGGTCTTCG | GTTTCCGTGT | TTCGTAAAGT | CTGGAAACGC | 2520
| GGAAGTCAGC | GCCCTGCACC | ATTATGTTCC | GGATCTGCAT | CGCAGGATGC | TGCTGGCTAC | 2580
| CCTGTGGAAC | ACCTACATCT | GTATTAACGA | AGCGCTGGCA | TTGACCCTGA | GTGATTTTTC | 2640
| TCTGGTCCCG | CCGCATCCAT | ACCGCCAGTT | GTTTACCCTC | ACAACGTTCC | AGTAACCGGG | 2700
| CATGTTCATC | ATCAGTAACC | CGTATCGTGA | GCATCCTCTC | TCGTTTCATC | GGTATCATTA | 2760
| CCCCCATGAA | CAGAAATTCC | CCCTTACACG | GAGGCATCAA | GTGACCAAAC | AGGAAAAAAC | 2820
| CGCCCTTAAC | ATGGCCCGCT | TTATCAGAAG | CCAGACATTA | ACGCTTCTGG | AGAAACTCAA | 2880
| CGAGCTGGAC | GCGGATGAAC | AGGCAGACAT | CTGTGAATCG | CTTCACGACC | ACGCTGATGA | 2940
| GCTTTACCGC | AGCTGCCTCG | CGCGTTTCGG | TGATGACGGT | GAAAACCTCT | GACACATGCA | 3000
| GCTCCCGGAG | ACGGTCACAG | CTTGTCTGTA | AGCGGATGCC | GGGAGCAGAC | AAGCCCGTCA | 3060
| GGGCGCGTCA | GCGGGTGTTG | GCGGGTGTCG | GGGCGCAGCC | ATGACCCAGT | CACGTAGCGA | 3120

-continued

```
TAGCGGAGTG TATACTGGCT TAACTATGCG GCATCAGAGC AGATTGTACT GAGAGTGCAC     3180
CATATATGCG GTGTGAAATA CCGCACAGAT GCGTAAGGAG AAAATACCGC ATCAGGCGCT     3240
CTTCCGCTTC CTCGCTCACT GACTCGCTGC GCTCGGTCGT TCGGCTGCGG CGAGCGGTAT     3300
CAGCTCACTC AAAGGCGGTA ATACGGTTAT CCACAGAATC AGGGGATAAC GCAGGAAAGA     3360
ACATGTGAGC AAAAGGCCAG CAAAAGGCCA GGAACCGTAA AAAGGCCGCG TTGCTGGCGT     3420
TTTTCCATAG GCTCCGCCCC CCTGACGAGC ATCACAAAAA TCGACGCTCA AGTCAGAGGT     3480
GGCGAAACCC GACAGGACTA TAAAGATACC AGGCGTTTCC CCCTGGAAGC TCCCTCGTGC     3540
GCTCTCCTGT TCCGACCCTG CCGCTTACCG GATACCTGTC CGCCTTTCTC CCTTCGGGAA     3600
GCGTGGCGCT TTCTCATAGC TCACGCTGTA GGTATCTCAG TTCGGTGTAG TCGTTCGCT      3660
CCAAGCTGGG CTGTGTGCAC GAACCCCCCG TTCAGCCCGA CCGCTGCGCC TTATCCGGTA     3720
ACTATCGTCT TGAGTCCAAC CCGGTAAGAC ACGACTTATC GCCACTGGCA GCAGCCACTG     3780
GTAACAGGAT TAGCAGAGCG AGGTATGTAG GCGGTGCTAC AGAGTTCTTG AAGTGGTGGC     3840
CTAACTACGG CTACACTAGA AGGACAGTAT TTGGTATCTG CGCTCTGCTG AAGCCAGTTA     3900
CCTTCGGAAA AAGAGTTGGT AGCTCTTGAT CCGGCAAACA AACCACCGCT GGTAGCGGTG     3960
GTTTTTTTGT TTGCAAGCAG CAGATTACGC GCAGAAAAAA AGGATCTCAA GAAGATCCTT     4020
TGATCTTTTC TACGGGGTCT GACGCTCAGT GGAACGAAAA CTCACGTTAA GGGATTTTGG     4080
TCATGAGATT ATCAAAAAGG ATCTTCACCT AGATCCTTTT AAATTAAAAA TGAAGTTTTA     4140
AATCAATCTA AAGTATATAT GAGTAAACTT GGTCTGACAG TTACCAATGC TTAATCAGTG     4200
AGGCACCTAT CTCAGCGATC TGTCTATTTC GTTCATCCAT AGTTGCCTGA CTCCCCGTCG     4260
TGTAGATAAC TACGATACGG GAGGGCTTAC CATCTGGCCC CAGTGCTGCA ATGATACCGC     4320
GAGACCCACG CTCACCGGCT CCAGATTTAT CAGCAATAAA CCAGCCAGCC GGAAGGGCCG     4380
AGCGCAGAAG TGGTCCTGCA ACTTTATCCG CCTCCATCCA GTCTATTAAT TGTTGCCGGG     4440
AAGCTAGAGT AAGTAGTTCG CCAGTTAATA GTTTGCGCAA CGTTGTTGCC ATTGCTGCAG     4500
GCATCGTGGT GTCACGCTCG TCGTTTGGTA TGGCTTCATT CAGCTCCGGT TCCCAACGAT     4560
CAAGGCGAGT TACATGATCC CCCATGTTGT GCAAAAAAGC GGTTAGCTCC TTCGGTCCTC     4620
CGATCGTTGT CAGAAGTAAG TTGGCCGCAG TGTTATCACT CATGGTTATG GCAGCACTGC     4680
ATAATTCTCT TACTGTCATG CCATCCGTAA GATGCTTTTC TGTGACTGGT GAGTACTCAA     4740
CCAAGTCATT CTGAGAATAG TGTATGCGGC GACCGAGTTG CTCTTGCCCG GCGTCAACAC     4800
GGGATAATAC CGCGCCACAT AGCAGAACTT TAAAAGTGCT CATCATTGGA AAACGTTCTT     4860
CGGGGCGAAA ACTCTCAAGG ATCTTACCGC TGTTGAGATC CAGTTCGATG TAACCCACTC     4920
GTGCACCCAA CTGATCTTCA GCATCTTTTA CTTTCACCAG CGTTTCTGGG TGAGCAAAAA     4980
CAGGAAGGCA AAATGCCGCA AAAAAGGGAA TAAGGGCGAC ACGGAAATGT TGAATACTCA     5040
TACTCTTCCT TTTTCAATAT TATTGAAGCA TTTATCAGGG TTATTGTCTC ATGAGCGGAT     5100
ACATATTTGA ATGTATTTAG AAAAATAAAC AAATAGGGGT TCCGCGCACA TTTCCCCGAA     5160
AAGTGCCACC TGACGTCTAA GAAACCATTA TTATCATGAC ATTAACCTAT AAAAATAGGC     5220
GTATCACGAG GCCCTTTCGT CTTCAAGAA                                      5249
```

( 2 ) INFORMATION FOR SEQ ID NO: 4:

( i ) SEQUENCE CHARACTERISTICS:
        ( A ) LENGTH: 5249 base pairs
        ( B ) TYPE: nucleic acid
        ( C ) STRANDEDNESS: single (D) TOPOLOGY: linear (xi) SEQUENCE DESCRIPTION: SEQ ID NO: 4:

```
TTCAGATCTA AAAGCCATTG ACTCAGCAAG GGTTGACCGT ATAATTCACG CGATTACACC       60
GCATTGCGGT ATCAACGCGC CCTTAGCTCA GTTGGATAGA GCAACGACCT TCTAAGTCGT      120
GGGCCGCAGG TTCGAATCCT GCAGGGCGCG CCATTACAAT TCAATCAGTT ACGCCTTCTT      180
TATATCCTCC ATAATTTCAG AGTGGGACAT ATTTGGGACA TTATCACCAA AAATGTCGTC      240
TATTTTCCTC GCATGCTCTG TCACATGTGA ATTCTCATGT TTGACAGCTT ATCATCGATA      300
AGCTTTAATG CGGTAGTTTA TCACAGTTAA ATTGCTAACG CAGTCAGGCA CCGTGTATGA      360
AATCTAACAA TGCGCTCATC GTCATCCTCG GCACCGTCAC CCTGGATGCT GTAGGCATAG      420
GCTTGGTTAT GCCGGTACTG CCGGGCCTCT TGCGGGATAT CGTCCATTCC GACAGCATCG      480
CCAGTCACTA TGGCGTGCTG CTAGTCCAGT AATGACCTCA GAACTCCATC TGGATTTGTT      540
CAGAACGCTC GGTTGCCGCC GGGCGTTTTT TATTGGTGAG AATCGCAGCA ACTTGTCGCG      600
CCAATCGAGC CATGTCGTCG TCAACGACCC CCCATTCAAG AACAGCAAGC AGCATTGAGA      660
ACTTTGGAAT CCAGTCCCTC TTCCACCTGC TGACTAGCGC TATATGCGTT GATGCAATTT      720
CTATGCGCAC CCGTTCTCGG AGCACTGTCC GACCGCTTTG CCGCCGCCC AGTCCTGCTC       780
GCTTCGCTAC TTGGAGCCAC TATCGACTAC GCGATCATGG CGACCACACC CGTCCTGTGG      840
ATCTCTCACC TACCAAACAA TGCCCCCCTG CAAAAAATAA ATTCATATAA AAAACATACA      900
GATAACCATC TGCGGTGATA AATTATCTCT GGCGGTGTTG ACATAAATAC CACTGGCGGT      960
GATACTGAGC ACATCAGCAG GACGCACTGA CCACCATGAA GGTGACGCTC TTAAAAATTA     1020
AGCCCTGAAG AAGGGCAGCA TTCAAAGCAG AAGGCTTTGG GGTGTGTGAT ACGAAACGAA     1080
GCATTGGCCG TAAGTGCGAT TCCGGATTAG CTGCCAATGT GCCAATCGCG GGGGTTTTC      1140
GTTCAGGACT ACAACTGCCA CACACCACCA AAGCTAACTG ACAGGAGAAT CCAGATGGAT     1200
GCACAAACAC GCCGCCGCGA ACGTCGCGCA GAGAAACAGG CTCAATGGAA AGCAGCAAAT     1260
CCCCTGTTGG TTGGGGTAAG CGCAAAACCA GTTCCGAAAG ATTTTTTAA CTATAAACGC      1320
TGATGGAAGC GTTTATGCGG AAGAGGTAAA GCCCTTCCCG AGTAACAAAA AAACAACAGC     1380
ATAAATAACC CCGCTCTTAC ACATTCCAGC CCTGAAAAAG GGCATCAAAT TAAACCACAC     1440
CTATGGTGTA TGCATTTATT TGCATACATT CAATCAATTG TTATCTAAGG AAATACTTAC     1500
ATATGATATC TAGAGGATCC CGGGTACCGA GCTCGTCGAC CGATGCCCTT GAGAGCCTTC     1560
AACCCAGTCA GCTCCTTCCG GTGGGCGCGG GGCATGACTA TCGTCGCCGC ACTTATGACT     1620
GTCTTCTTTA TCATGCAACT CGTAGGACAG GTGCCGGCAG CGCTCTGGGT CATTTTCGGC     1680
GAGGACCGCT TTCGCTGGAG CGCGACGATG ATCGGCCTGT CGCTTGCGGT ATTCGGAATC     1740
TTGCACGCCC TCGCTCAAGC CTTCGTCACT GGTCCCGCCA CCAAACGTTT CGGCGAGAAG     1800
CAGGCCATTA TCGCCGGCAT GGCGGCCGAC GCGCTGGGCT ACGTCTTGCT GGCGTTCGCG     1860
ACGCGAGGCT GGATGGCCTT CCCCATTATG ATTCTTCTCG CTTCCGGCGG CATCGGGATG     1920
CCCGCGTTGC AGGCCATGCT GTCCAGGCAG GTAGATGACG ACCATCAGGG ACAGCTTCAA     1980
GGATCGCTCG CGGCTCTTAC CAGCCTAACT TCGATCACTG GACCGCTGAT CGTCACGGCG     2040
ATTTATGCCG CCTCGGCGAG CACATGGAAC GGGTTGGCAT GGATTGTAGG CGCCGCCCTA     2100
TACCTTGTCT GCCTCCCCGC GTTGCGTCGC GGTGCATGGA GCCGGGCCAC CTCGACCTGA     2160
ATGGAAGCCG GCGGCACCTC GCTAACGGAT TCACCACTCC AAGAATTGGA GCCAATCAAT     2220
TCTTGCGGAG AACTGTGAAT GCGCAAACCA ACCCTTGGCA GAACATATCC ATCGCGTCCG     2280
```

| | | | | | | |
|---|---|---|---|---|---|---|
| CCATCTCCAG | CAGCCGCACG | CGGCGCATCT | CGGGCAGCGT | TGGGTCCTGG | CCACGGGTGC | 2340 |
| GCATGATCGT | GCTCCTGTCG | TTGAGGACCC | GGCTAGGCTG | GCGGGGTTGC | CTTACTGGTT | 2400 |
| AGCAGAATGA | ATCACCGATA | CGCGAGCGAA | CGTGAAGCGA | CTGCTGCTGC | AAAACGTCTG | 2460 |
| CGACCTGAGC | AACAACATGA | ATGGTCTTCG | GTTTCCGTGT | TTCGTAAAGT | CTGGAAACGC | 2520 |
| GGAAGTCAGC | GCCCTGCACC | ATTATGTTCC | GGATCTGCAT | CGCAGGATGC | TGCTGGCTAC | 2580 |
| CCTGTGGAAC | ACCTACATCT | GTATTAACGA | AGCGCTGGCA | TTGACCCTGA | GTGATTTTTC | 2640 |
| TCTGGTCCCG | CCGCATCCAT | ACCGCCAGTT | GTTTACCCTC | ACAACGTTCC | AGTAACCGGG | 2700 |
| CATGTTCATC | ATCAGTAACC | CGTATCGTGA | GCATCCTCTC | TCGTTTCATC | GGTATCATTA | 2760 |
| CCCCCATGAA | CAGAAATTCC | CCCTTACACG | GAGGCATCAA | GTGACCAAAC | AGGAAAAAAC | 2820 |
| CGCCCTTAAC | ATGGCCCGCT | TTATCAGAAG | CCAGACATTA | ACGCTTCTGG | AGAAACTCAA | 2880 |
| CGAGCTGGAC | GCGGATGAAC | AGGCAGACAT | CTGTGAATCG | CTTCACGACC | ACGCTGATGA | 2940 |
| GCTTTACCGC | AGCTGCCTCG | CGCGTTTCGG | TGATGACGGT | GAAAACCTCT | GACACATGCA | 3000 |
| GCTCCCGGAG | ACGGTCACAG | CTTGTCTGTA | AGCGGATGCC | GGGAGCAGAC | AAGCCCGTCA | 3060 |
| GGGCGCGTCA | GCGGGTGTTG | GCGGGTGTCG | GGGCGCAGCC | ATGACCCAGT | CACGTAGCGA | 3120 |
| TAGCGGAGTG | TATACTGGCT | TAACTATGCG | GCATCAGAGC | AGATTGTACT | GAGAGTGCAC | 3180 |
| CATATATGCG | GTGTGAAATA | CCGCACAGAT | GCGTAAGGAG | AAAATACCGC | ATCAGGCGCT | 3240 |
| CTTCCGCTTC | CTCGCTCACT | GACTCGCTGC | GCTCGGTCGT | TCGGCTGCGG | CGAGCGGTAT | 3300 |
| CAGCTCACTC | AAAGGCGGTA | ATACGGTTAT | CCACAGAATC | AGGGGATAAC | GCAGGAAAGA | 3360 |
| ACATGTGAGC | AAAAGGCCAG | CAAAAGGCCA | GGAACCGTAA | AAAGGCCGCG | TTGCTGGCGT | 3420 |
| TTTTCCATAG | GCTCCGCCCC | CCTGACGAGC | ATCACAAAAA | TCGACGCTCA | AGTCAGAGGT | 3480 |
| GGCGAAACCC | GACAGGACTA | TAAAGATACC | AGGCGTTTCC | CCCTGGAAGC | TCCCTCGTGC | 3540 |
| GCTCTCCTGT | TCCGACCCTG | CCGCTTACCG | GATACCTGTC | CGCCTTTCTC | CCTTCGGGAA | 3600 |
| GCGTGGCGCT | TTCTCATAGC | TCACGCTGTA | GGTATCTCAG | TTCGGTGTAG | GTCGTTCGCT | 3660 |
| CCAAGCTGGG | CTGTGTGCAC | GAACCCCCCG | TTCAGCCCGA | CCGCTGCGCC | TTATCCGGTA | 3720 |
| ACTATCGTCT | TGAGTCCAAC | CCGGTAAGAC | ACGACTTATC | GCCACTGGCA | GCAGCCACTG | 3780 |
| GTAACAGGAT | TAGCAGAGCG | AGGTATGTAG | GCGGTGCTAC | AGAGTTCTTG | AAGTGGTGGC | 3840 |
| CTAACTACGG | CTACACTAGA | AGGACAGTAT | TTGGTATCTG | CGCTCTGCTG | AAGCCAGTTA | 3900 |
| CCTTCGGAAA | AAGAGTTGGT | AGCTCTTGAT | CCGGCAAACA | AACCACCGCT | GGTAGCGGTG | 3960 |
| GTTTTTTTGT | TTGCAAGCAG | CAGATTACGC | GCAGAAAAAA | AGGATCTCAA | GAAGATCCTT | 4020 |
| TGATCTTTTC | TACGGGGTCT | GACGCTCAGT | GGAACGAAAA | CTCACGTTAA | GGGATTTTGG | 4080 |
| TCATGAGATT | ATCAAAAAGG | ATCTTCACCT | AGATCCTTTT | AAATTAAAAA | TGAAGTTTTA | 4140 |
| AATCAATCTA | AAGTATATAT | GAGTAAACTT | GGTCTGACAG | TTACCAATGC | TTAATCAGTG | 4200 |
| AGGCACCTAT | CTCAGCGATC | TGTCTATTTC | GTTCATCCAT | AGTTGCCTGA | CTCCCCGTCG | 4260 |
| TGTAGATAAC | TACGATACGG | GAGGGCTTAC | CATCTGGCCC | CAGTGCTGCA | ATGATACCGC | 4320 |
| GAGACCCACG | CTCACCGGCT | CCAGATTTAT | CAGCAATAAA | CCAGCCAGCC | GGAAGGGCCG | 4380 |
| AGCGCAGAAG | TGGTCCTGCA | ACTTTATCCG | CCTCCATCCA | GTCTATTAAT | TGTTGCCGGG | 4440 |
| AAGCTAGAGT | AAGTAGTTCG | CCAGTTAATA | GTTTGCGCAA | CGTTGTTGCC | ATTGCTGCAG | 4500 |
| GCATCGTGGT | GTCACGCTCG | TCGTTTGGTA | TGGCTTCATT | CAGCTCCGGT | TCCCAACGAT | 4560 |
| CAAGGCGAGT | TACATGATCC | CCCATGTTGT | GCAAAAAAGC | GGTTAGCTCC | TTCGGTCCTC | 4620 |
| CGATCGTTGT | CAGAAGTAAG | TTGGCCGCAG | TGTTATCACT | CATGGTTATG | GCAGCACTGC | 4680 |

```
ATAATTCTCT  TACTGTCATG  CCATCCGTAA  GATGCTTTTC  TGTGACTGGT  GAGTACTCAA      4740

CCAAGTCATT  CTGAGAATAG  TGTATGCGGC  GACCGAGTTG  CTCTTGCCCG  GCGTCAACAC      4800

GGGATAATAC  CGCGCCACAT  AGCAGAACTT  TAAAAGTGCT  CATCATTGGA  AAACGTTCTT      4860

CGGGGCGAAA  ACTCTCAAGG  ATCTTACCGC  TGTTGAGATC  CAGTTCGATG  TAACCCACTC      4920

GTGCACCCAA  CTGATCTTCA  GCATCTTTTA  CTTTCACCAG  CGTTTCTGGG  TGAGCAAAAA      4980

CAGGAAGGCA  AAATGCCGCA  AAAAGGGAA   TAAGGGCGAC  ACGGAAATGT  TGAATACTCA      5040

TACTCTTCCT  TTTTCAATAT  TATTGAAGCA  TTTATCAGGG  TTATTGTCTC  ATGAGCGGAT      5100

ACATATTTGA  ATGTATTTAG  AAAAATAAAC  AAATAGGGGT  TCCGCGCACA  TTTCCCCGAA      5160

AAGTGCCACC  TGACGTCTAA  GAAACCATTA  TTATCATGAC  ATTAACCTAT  AAAAATAGGC      5220

GTATCACGAG  GCCCTTTCGT  CTTCAAGAA                                            5249
```

( 2 ) INFORMATION FOR SEQ ID NO: 5:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 5:

```
GGGGTACCAT  ATGATTTTAG  ATGTGGATTA  CATAAC                                   36
```

( 2 ) INFORMATION FOR SEQ ID NO: 6:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 6:

```
TCCCCCGGGC  TAGGATTTTT  TAATGTTAAG  CCA                                      33
```

( 2 ) INFORMATION FOR SEQ ID NO: 7:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 7:

```
AAGGATCCTG  ACATTATAGT  TACTTATAAT  GGAGACTCAT  TCGCCTTCCC                   50
```

( 2 ) INFORMATION FOR SEQ ID NO: 8:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 8:

```
GGAATTCTTT  CCCGAGTTCA  TAAG                                                 24
```

( 2 ) INFORMATION FOR SEQ ID NO: 9:

( i ) SEQUENCE CHARACTERISTICS:
        ( A ) LENGTH: 95 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 9:

GCTATCCTGG ACGTTGACTA CATCACCGAA GAAGGTAAGC CGGTTATCCG     50

TCTGTTCAAA AAAGAAAACG GTAAATTCAA AATCGAACAC GACCG     95

( 2 ) INFORMATION FOR SEQ ID NO: 10:

( i ) SEQUENCE CHARACTERISTICS:
        ( A ) LENGTH: 95 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 10:

ACCGGTGATT TTTTTAACTT CTTCGATTTT AGAGTCGTCA CGCAGCAGAG     50

CGTAGATGTA CGGACGGAAG GTACGGTCGT GTTCGATTTT GAATT     95

( 2 ) INFORMATION FOR SEQ ID NO: 11:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 11:

GGGGTACCAT ATGGCTATCC TGGACGTTGA CTACATC     37

( 2 ) INFORMATION FOR SEQ ID NO: 12:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 12:

GGGGTACCAC CGGTGATTTT TTTAACTTCT TC     32

( 2 ) INFORMATION FOR SEQ ID NO: 13:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 13:

AAATAACCGG TGAACGTCAT GGAAAGATTG TG     32

( 2 ) INFORMATION FOR SEQ ID NO: 14:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 14:

CCTTTGCTTC ATTTTCATCT G     21

( 2 ) INFORMATION FOR SEQ ID NO: 15:

( i ) SEQUENCE CHARACTERISTICS:
        ( A ) LENGTH: 50 base pairs
        ( B ) TYPE: nucleic acid ( C ) STRANDEDNESS: single
( D ) TOPOLOGY: linear ( x i ) SEQUENCE DESCRIPTION: SEQ ID NO: 15:

AGTAGGCCAC AAGTTCTGCA AGGACATCCC TGGTTTTATA CCAAGTCTCT                50

( 2 ) INFORMATION FOR SEQ ID NO: 16:

( i ) SEQUENCE CHARACTERISTICS:
( A ) LENGTH: 50 base pairs
( B ) TYPE: nucleic acid
( C ) STRANDEDNESS: single
( D ) TOPOLOGY: linear ( x i ) SEQUENCE DESCRIPTION: SEQ ID NO: 16:

TGGGACATTT GCTCGAGGAA AGACAAAAGA TTAAGACAAA AATGAAGGAA                50

( 2 ) INFORMATION FOR SEQ ID NO: 17:

( i ) SEQUENCE CHARACTERISTICS:
( A ) LENGTH: 50 base pairs
( B ) TYPE: nucleic acid
( C ) STRANDEDNESS: single
( D ) TOPOLOGY: linear ( x i ) SEQUENCE DESCRIPTION: SEQ ID NO: 17:

ACTCAAGATC CTATAGAAAA AATACTCCTT GACTATAGAC AAAAAGCGAT                50

( 2 ) INFORMATION FOR SEQ ID NO: 18:

( i ) SEQUENCE CHARACTERISTICS:
( A ) LENGTH: 50 base pairs
( B ) TYPE: nucleic acid
( C ) STRANDEDNESS: single
( D ) TOPOLOGY: linear ( x i ) SEQUENCE DESCRIPTION: SEQ ID NO: 18:

AAAACTCTTA GCAAATTCTT TCTACGGATA TTATGGCTAT GCAAAAGCGC                50

( 2 ) INFORMATION FOR SEQ ID NO: 19:

( i ) SEQUENCE CHARACTERISTICS:
( A ) LENGTH: 50 base pairs
( B ) TYPE: nucleic acid
( C ) STRANDEDNESS: single
( D ) TOPOLOGY: linear ( x i ) SEQUENCE DESCRIPTION: SEQ ID NO: 19:

GCTGGTACTG TAAGGAGTGT GCTGAGAGCG TTACTGCCTG GGGAAGAAAG                50

( 2 ) INFORMATION FOR SEQ ID NO: 20:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( x i ) SEQUENCE DESCRIPTION: SEQ ID NO: 20:

TACATCGAGT TAGTATGGAA GGAGCT                                          26

( 2 ) INFORMATION FOR SEQ ID NO: 21:

( i ) SEQUENCE CHARACTERISTICS:
( A ) LENGTH: 50 base pairs
( B ) TYPE: nucleic acid
( C ) STRANDEDNESS: single
( D ) TOPOLOGY: linear ( x i ) SEQUENCE DESCRIPTION: SEQ ID NO: 21:

CCTTCCATAC TAACTCGATG TACTTTCTTC CCCAGGCAGT AACGCTCTCA  50

( 2 ) INFORMATION FOR SEQ ID NO: 22:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 22:

GCACACTCCT TACAGTACCA GCGCGCTTTT GCATAGCCAT AATATCCGTA  50

( 2 ) INFORMATION FOR SEQ ID NO: 23:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 23:

GAAAGAATTT GCTAAGAGTT TTATCGCTTT TTGTCTATAG TCAAGGAGTA  50

( 2 ) INFORMATION FOR SEQ ID NO: 24:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 24:

TTTTTCTAT AGGATCTTGA GTTTCCTTCA TTTTTGTCTT AATCTTTTGT  50

( 2 ) INFORMATION FOR SEQ ID NO: 25:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 25:

CTTTCCTCTA ACAAATGTCC CAAGAGACTT GGTATAAAAC CAGGGATGTC  50

( 2 ) INFORMATION FOR SEQ ID NO: 26:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 26:

CTTGCAGAAC TTGTGGCCTA C  21

( 2 ) INFORMATION FOR SEQ ID NO: 27:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 27:

TCGCTCCTCA AGTAGGCCAC AAGTTCTGCA AGGACATCCC                    40

( 2 ) INFORMATION FOR SEQ ID NO: 28:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 28:

TCTTCGAGCT CCTTCCATAC TAACTCGATG TACTTTCTTC                    40

( 2 ) INFORMATION FOR SEQ ID NO: 29:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 29:

AAAACTCTTA TACAATTCTT TCTACGGATA TTATGGCTAT GCAAAAGCGC         50

( 2 ) INFORMATION FOR SEQ ID NO: 30:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 30:

GAAAGAATTG TATAAGAGTT TTATCGCTTT TTGTCTATAG TCAAGGAGTA         50

( 2 ) INFORMATION FOR SEQ ID NO: 31:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 31:

AAAACTCTTA GCATACTCTT TCTACGGATA TTATGGCTAT GCAAAAGCGC         50

( 2 ) INFORMATION FOR SEQ ID NO: 32:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 32:

GAAAGAGTAT GCTAAGAGTT TTATCGCTTT TTGTCTATAG TCAAGGAGTA         50

( 2 ) INFORMATION FOR SEQ ID NO: 33:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 33:

AAAACTCTTA GCATACAATT CTTTCTACGG ATATTATGGC TATGCAAAAG CGC     53

(2) INFORMATION FOR SEQ ID NO: 34:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (xi) SEQUENCE DESCRIPTION: SEQ ID NO: 34:

```
GAAAGAATTG TATGCTAAGA GTTTTATCGC TTTTTGTCTA TAGTCAAGGA GTA            53
```

(2) INFORMATION FOR SEQ ID NO: 35:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (xi) SEQUENCE DESCRIPTION: SEQ ID NO: 35:

```
AAAACCATC AACTACGGTG TTCTCTACGG ATATTATGGC TATGCAAAAG CGC             53
```

(2) INFORMATION FOR SEQ ID NO: 36:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (xi) SEQUENCE DESCRIPTION: SEQ ID NO: 36:

```
GAGAACACCG TAGTTGATGG TTTTTATCGC TTTTTGTCTA TAGTCAAGGA GTA            53
```

(2) INFORMATION FOR SEQ ID NO: 37:

(i) SEQUENCE CHARACTERISTICS:
        (A) LENGTH: 776 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 37:

```
Met Ile Leu Asp Val Asp Tyr Ile Thr Glu Glu Gly Lys Pro Val Ile
 1               5                  10                  15
Arg Leu Phe Lys Lys Glu Asn Gly Lys Phe Lys Ile Glu His Asp Arg
            20                  25                  30
Thr Phe Arg Pro Tyr Ile Tyr Ala Leu Leu Arg Asp Asp Ser Lys Ile
            35                  40                  45
Glu Glu Val Lys Lys Ile Thr Gly Glu Arg His Gly Lys Ile Val Arg
    50                  55                  60
Ile Val Asp Val Glu Lys Val Glu Lys Lys Phe Leu Gly Lys Pro Ile
65                  70                  75                  80
Thr Val Trp Lys Leu Tyr Leu Glu His Pro Gln Asp Val Pro Thr Ile
                85                  90                  95
Arg Glu Lys Val Arg Glu His Pro Ala Val Val Asp Ile Phe Glu Tyr
               100                 105                 110
Asp Ile Pro Phe Ala Lys Arg Tyr Leu Ile Asp Lys Gly Leu Ile Pro
           115                 120                 125
Met Glu Gly Glu Glu Glu Leu Lys Ile Leu Ala Phe Asp Ile Glu Thr
       130                 135                 140
```

-continued

| | | | | | | | | | | | | | | |
|---|---|---|---|---|---|---|---|---|---|---|---|---|---|---|
| Leu | Tyr | His | Glu | Gly | Glu | Phe | Gly | Lys | Gly | Pro | Ile | Ile | Met | Ile |
| 145 | | | | 150 | | | | 155 | | | | | | 160 |
| Ser | Tyr | Ala | Asp | Glu | Asn | Glu | Ala | Lys | Val | Ile | Thr | Trp | Lys | Asn | Ile |
| | | | | 165 | | | | 170 | | | | | 175 | |
| Asp | Leu | Pro | Tyr | Val | Glu | Val | Val | Ser | Ser | Glu | Arg | Glu | Met | Ile | Lys |
| | | | 180 | | | | | 185 | | | | | 190 | |
| Arg | Phe | Leu | Arg | Ile | Ile | Arg | Glu | Lys | Asp | Pro | Asp | Ile | Ile | Val | Thr |
| | | 195 | | | | | 200 | | | | 205 | | | | |
| Tyr | Asn | Gly | Asp | Ser | Phe | Asp | Phe | Pro | Tyr | Leu | Ala | Lys | Arg | Ala | Glu |
| | 210 | | | | 215 | | | | | 220 | | | | | |
| Lys | Leu | Gly | Ile | Lys | Leu | Thr | Ile | Gly | Arg | Asp | Gly | Ser | Glu | Pro | Lys |
| 225 | | | | 230 | | | | 235 | | | | | | 240 |
| Met | Gln | Arg | Ile | Gly | Asp | Met | Thr | Ala | Val | Glu | Val | Lys | Gly | Arg | Ile |
| | | | 245 | | | | 250 | | | | | 255 | | | |
| His | Phe | Asp | Leu | Tyr | His | Val | Ile | Thr | Arg | Thr | Ile | Asn | Leu | Pro | Thr |
| | | | 260 | | | | 265 | | | | 270 | | | | |
| Tyr | Thr | Leu | Glu | Ala | Val | Tyr | Glu | Ala | Ile | Phe | Gly | Lys | Pro | Lys | Glu |
| | | 275 | | | | 280 | | | | 285 | | | | | |
| Lys | Val | Tyr | Ala | Asp | Glu | Ile | Ala | Lys | Ala | Trp | Glu | Ser | Gly | Glu | Asn |
| | 290 | | | | 295 | | | | 300 | | | | | | |
| Leu | Glu | Arg | Val | Ala | Lys | Tyr | Ser | Met | Glu | Asp | Ala | Lys | Ala | Thr | Tyr |
| 305 | | | | 310 | | | | 315 | | | | | | 320 |
| Glu | Leu | Gly | Lys | Glu | Phe | Leu | Pro | Met | Glu | Ile | Gln | Leu | Ser | Arg | Leu |
| | | | 325 | | | | 330 | | | | | 335 | | | |
| Val | Gly | Gln | Pro | Leu | Trp | Asp | Val | Ser | Arg | Ser | Ser | Thr | Gly | Asn | Leu |
| | | 340 | | | | | 345 | | | | 350 | | | | |
| Val | Glu | Trp | Phe | Leu | Leu | Arg | Lys | Ala | Tyr | Glu | Arg | Asn | Glu | Val | Ala |
| | | 355 | | | | | 360 | | | | 365 | | | | |
| Pro | Asn | Lys | Pro | Ser | Glu | Glu | Tyr | Gln | Arg | Arg | Leu | Arg | Glu | Ser |
| | 370 | | | | 375 | | | | 380 | | | | | |
| Tyr | Thr | Gly | Gly | Phe | Val | Lys | Glu | Pro | Glu | Lys | Gly | Leu | Trp | Glu | Asn |
| 385 | | | | 390 | | | | 395 | | | | | 400 | | |
| Ile | Val | Tyr | Leu | Asp | Phe | Arg | Ala | Leu | Tyr | Pro | Ser | Ile | Ile | Ile | Thr |
| | | | 405 | | | | 410 | | | | 415 | | | | |
| His | Asn | Val | Ser | Pro | Asp | Thr | Leu | Asn | Leu | Glu | Gly | Cys | Lys | Asn | Tyr |
| | | | 420 | | | | 425 | | | | 430 | | | | |
| Asp | Ile | Ala | Pro | Gln | Val | Gly | His | Lys | Phe | Cys | Lys | Asp | Ile | Pro | Gly |
| | | 435 | | | | 440 | | | | 445 | | | | | |
| Phe | Ile | Pro | Ser | Leu | Leu | Gly | His | Leu | Leu | Glu | Glu | Arg | Gln | Lys | Ile |
| | 450 | | | | 455 | | | | 460 | | | | | | |
| Lys | Thr | Lys | Met | Lys | Glu | Thr | Gln | Asp | Pro | Ile | Glu | Lys | Ile | Leu | Leu |
| 465 | | | | 470 | | | | 475 | | | | | | 480 |
| Asp | Tyr | Arg | Gln | Lys | Ala | Ile | Lys | Leu | Leu | Ala | Asn | Ser | Phe | Tyr | Gly |
| | | | 485 | | | | 490 | | | | 495 | | | | |
| Tyr | Tyr | Gly | Tyr | Ala | Lys | Ala | Arg | Trp | Tyr | Cys | Lys | Glu | Cys | Ala | Glu |
| | | | 500 | | | | 505 | | | | 510 | | | | |
| Ser | Val | Thr | Ala | Trp | Gly | Arg | Lys | Tyr | Ile | Glu | Leu | Val | Trp | Lys | Glu |
| | | 515 | | | | 520 | | | | 525 | | | | | |
| Leu | Glu | Glu | Lys | Phe | Gly | Phe | Lys | Val | Leu | Tyr | Ile | Asp | Thr | Asp | Gly |
| | | | 530 | | | | 535 | | | | 540 | | | | |
| Leu | Tyr | Ala | Thr | Ile | Pro | Gly | Gly | Glu | Ser | Glu | Glu | Ile | Lys | Lys | Lys |
| 545 | | | | 550 | | | | 555 | | | | | | 560 |
| Ala | Leu | Glu | Phe | Val | Lys | Tyr | Ile | Asn | Ser | Lys | Leu | Pro | Gly | Leu | Leu |
| | | | 565 | | | | 570 | | | | 575 | | | | |

| | | | | | | | | | | | | | | |
|---|---|---|---|---|---|---|---|---|---|---|---|---|---|---|
| Glu | Leu | Glu | Tyr 580 | Glu | Gly | Phe | Tyr 585 | Lys | Arg | Gly | Phe | Phe 590 | Val | Thr | Lys |
| Lys | Arg | Tyr 595 | Ala | Val | Ile | Asp 600 | Glu | Gly | Lys | Val | Ile 605 | Thr | Arg | Gly |
| Leu | Glu 610 | Ile | Val | Arg | Arg | Asp 615 | Trp | Ser | Glu | Ile | Ala 620 | Lys | Glu | Thr | Gln |
| Ala 625 | Arg | Val | Leu | Glu | Thr 630 | Ile | Leu | Lys | His | Gly 635 | Asp | Val | Glu | Glu | Ala 640 |
| Val | Arg | Ile | Val | Lys 645 | Glu | Val | Ile | Gln | Lys 650 | Leu | Ala | Asn | Tyr | Glu 655 | Ile |
| Pro | Pro | Glu | Lys 660 | Leu | Ala | Ile | Tyr | Glu 665 | Gln | Ile | Thr | Arg | Pro 670 | Leu | His |
| Glu | Tyr | Lys 675 | Ala | Ile | Gly | Pro | His 680 | Val | Ala | Val | Ala | Lys 685 | Lys | Leu | Ala |
| Ala | Lys 690 | Gly | Val | Lys | Ile | Lys 695 | Pro | Gly | Met | Val | Ile 700 | Gly | Tyr | Ile | Val |
| Leu 705 | Arg | Gly | Asp | Gly | Pro 710 | Ile | Ser | Asn | Arg | Ala 715 | Ile | Leu | Ala | Glu | Glu 720 |
| Tyr | Asp | Pro | Lys | Lys 725 | His | Lys | Tyr | Asp | Ala 730 | Glu | Tyr | Tyr | Ile | Glu 735 | Asn |
| Gln | Val | Leu | Pro 740 | Ala | Val | Leu | Arg | Ile 745 | Leu | Glu | Gly | Phe | Gly 750 | Tyr | Arg |
| Lys | Glu | Asp 755 | Leu | Arg | Tyr | Gln | Lys 760 | Thr | Arg | Gln | Val | Gly 765 | Leu | Thr | Ser |
| Trp | Leu 770 | Asn | Ile | Lys | Lys | Ser 775 | Glx | | | | | | | | |

( 2 ) INFORMATION FOR SEQ ID NO: 38:

( i ) SEQUENCE CHARACTERISTICS:
        ( A ) LENGTH: 2328 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 38:

```
ATGATTTTAG  ATGTGGATTA  CATAACTGAA  GAAGGAAAAC  CTGTTATTAG  GCTATTCAAA     60
AAAGAGAACG  GAAAATTTAA  GATAGAGCAT  GATAGAACTT  TTAGACCATA  CATTTACGCT    120
CTTCTCAGGG  ATGATTCAAA  GATTGAAGAA  GTTAAGAAAA  TAACGGGGGA  AAGGCATGGA    180
AAGATTGTGA  GAATTGTTGA  TGTAGAGAAG  GTTGAGAAAA  AGTTTCTCGG  CAAGCCTATT    240
ACCGTGTGGA  AACTTTATTT  GGAACATCCC  CAAGATGTTC  CCACTATTAG  AGAAAAAGTT    300
AGAGAACATC  CAGCAGTTGT  GGACATCTTC  GAATACGATA  TTCCATTTGC  AAAGAGATAC    360
CTCATCGACA  AAGGCCTAAT  ACCAATGGAG  GGGGAAGAAG  AGCTAAAGAT  TCTTGCCTTC    420
GATATAGAAA  CCCTCTATCA  CGAAGGAGAA  GAGTTTGGAA  AAGGCCCAAT  TATAATGATT    480
AGTTATGCAG  ATGAAAATGA  AGCAAGGTG   ATTACTTGGA  AAAACATAGA  TCTTCCATAC    540
GTTGAGGTTG  TATCAAGCGA  GAGAGAGATG  ATAAAGAGAT  TTCTCAGGAT  TATCAGGGAG    600
AAGGATCCTG  ACATTATAGT  TACTTATAAT  GGAGACTCAT  TCGACTTCCC  ATATTTAGCG    660
AAAAGGGCAG  AAAAACTTGG  GATTAAATTA  ACCATTGGAA  GAGATGGAAG  CGAGCCCAAG    720
ATGCAGAGAA  TAGGCGATAT  GACGGCTGTA  GAAGTCAAGG  GAAGAATACA  TTTCGACTTG    780
TATCATGTAA  TAACAAGGAC  AATAAATCTC  CCAACATACA  CACTAGAGGC  TGTATATGAA    840
GCAATTTTTG  GAAAGCCAAA  GGAGAAGGTA  TACGCCGACG  AGATAGCAAA  AGCCTGGGAA    900
```

-continued

| | | | | | | |
|---|---|---|---|---|---|---|
| AGTGGAGAGA | ACCTTGAGAG | AGTTGCCAAA | TACTCGATGG | AAGATGCAAA | GGCAACTTAT | 960 |
| GAACTCGGGA | AAGAATTCCT | TCCAATGGAA | ATTCAGCTTT | CAAGATTAGT | TGGACAACCT | 1020 |
| TTATGGGATG | TTTCAAGGTC | AAGCACAGGG | AACCTTGTAG | AGTGGTTCTT | ACTTAGGAAA | 1080 |
| GCCTACGAAA | GAAACGAAGT | AGCTCCAAAC | AAGCCAAGTG | AAGAGGAGTA | TCAAAGAAGG | 1140 |
| CTCAGGGAGA | GCTACACAGG | TGGATTCGTT | AAAGAGCCAG | AAAAGGGGTT | GTGGGAAAAC | 1200 |
| ATAGTATACC | TAGATTTTAG | AGCCCTATAT | CCCTCGATTA | TAATTACCCA | CAATGTTTCT | 1260 |
| CCCGATACTC | TAAATCTTGA | GGGATGCAAG | AACTATGATA | TCGCTCCTCA | AGTAGGCCAC | 1320 |
| AAGTTCTGCA | AGGACATCCC | TGGTTTTATA | CCAAGTCTCT | TGGGACATTT | GTTAGAGGAA | 1380 |
| AGACAAAAGA | TTAAGACAAA | AATGAAGGAA | ACTCAAGATC | CTATAGAAAA | AATACTCCTT | 1440 |
| GACTATAGAC | AAAAAGCGAT | AAAACTCTTA | GCAAATTCTT | TCTACGGATA | TTATGGCTAT | 1500 |
| GCAAAAGCAA | GATGGTACTG | TAAGGAGTGT | GCTGAGAGCG | TTACTGCCTG | GGGAAGAAAG | 1560 |
| TACATCGAGT | TAGTATGGAA | GGAGCTCGAA | GAAAGTTTG | GATTTAAAGT | CCTCTACATT | 1620 |
| GACACTGATG | GTCTCTATGC | AACTATCCCA | GGAGGAGAAA | GTGAGGAAAT | AAAGAAAAAG | 1680 |
| GCTCTAGAAT | TTGTAAAATA | CATAAATTCA | AAGCTCCCTG | GACTGCTAGA | GCTTGAATAT | 1740 |
| GAAGGGTTTT | ATAAGAGGGG | ATTCTTCGTT | ACGAAGAAGA | GGTATGCAGT | AATAGATGAA | 1800 |
| GAAGGAAAAG | TCATTACTCG | TGGTTTAGAG | ATAGTTAGGA | GAGATTGGAG | TGAAATTGCA | 1860 |
| AAAGAAACTC | AAGCTAGAGT | TTTGGAGACA | ATACTAAAAC | ACGGAGATGT | TGAAGAAGCT | 1920 |
| GTGAGAATAG | TAAAAGAAGT | AATACAAAAG | CTTGCCAATT | ATGAAATTCC | ACCAGAGAAG | 1980 |
| CTCGCAATAT | ATGAGCAGAT | AACAAGACCA | TTACATGAGT | ATAAGGCGAT | AGGTCCTCAC | 2040 |
| GTAGCTGTTG | CAAAGAAACT | AGCTGCTAAA | GGAGTTAAAA | TAAAGCCAGG | AATGGTAATT | 2100 |
| GGATACATAG | TACTTAGAGG | CGATGGTCCA | ATTAGCAATA | GGGCAATTCT | AGCTGAGGAA | 2160 |
| TACGATCCCA | AAAAGCACAA | GTATGACGCA | GAATATTACA | TTGAGAACCA | GGTTCTTCCA | 2220 |
| GCGGTACTTA | GGATATTGGA | GGGATTTGGA | TACAGAAAGG | AAGACCTCAG | ATACCAAAAG | 2280 |
| ACAAGACAAG | TCGGCCTAAC | TTCCTGGCTT | AACATTAAAA | AATCCTAG | | 2328 |